(12) United States Patent
Lyznik et al.

(10) Patent No.: US 7,608,752 B2
(45) Date of Patent: Oct. 27, 2009

(54) GENE TARGETING USING REPLICATING DNA MOLECULES

(75) Inventors: L. Alexander Lyznik, Johnston, IA (US); Xiaoxia Zhao, Fremont, CA (US); Isabelle S. Coats, Des Moines, IA (US); William J. Gordon-Kamm, Urbandale, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 253 days.

(21) Appl. No.: 11/533,381

(22) Filed: Sep. 20, 2006

(65) Prior Publication Data

US 2007/0016980 A1 Jan. 18, 2007

Related U.S. Application Data

(62) Division of application No. 10/138,546, filed on May 3, 2002, now Pat. No. 7,164,056.

(51) Int. Cl.
*C12N 15/83* (2006.01)
*C12N 15/82* (2006.01)
*C12N 15/34* (2006.01)

(52) U.S. Cl. .................. 800/280; 800/275; 800/278; 800/287; 435/463; 435/475; 435/468

(58) Field of Classification Search .................. None
See application file for complete search history.

(56) References Cited

U.S. PATENT DOCUMENTS

| | | | |
|---|---|---|---|
| 5,482,852 A | 1/1996 | Yoder et al. |
| 5,569,597 A | 10/1996 | Grimsley et al. |
| 5,658,772 A | 8/1997 | Odell et al. |
| 5,792,924 A | 8/1998 | Yoder et al. |
| 5,801,030 A | 9/1998 | McVey et al. |
| 5,811,653 A | 9/1998 | Turpen |
| 5,817,492 A | 10/1998 | Saito et al. |
| 6,077,992 A | 6/2000 | Yadav |
| 6,110,736 A | 8/2000 | Hodges et al. |
| 6,147,278 A | 11/2000 | Rogers et al. |
| 6,187,994 B1 | 2/2001 | Baszczynski et al. |
| 6,262,341 B1 | 7/2001 | Baszczynski et al. |
| 6,284,947 B1 | 9/2001 | Gordon-Kamm et al. |
| 6,300,545 B1 | 10/2001 | Baszczynski et al. |
| 6,331,661 B1 | 12/2001 | Baszczynski et al. |
| 6,376,234 B1 | 4/2002 | Grimsley et al. |
| 6,391,642 B1 | 5/2002 | Resnick et al. |
| 6,392,121 B1 | 5/2002 | Mason et al. |
| 6,395,487 B1 | 5/2002 | Bradley et al. |
| 6,413,777 B1 | 7/2002 | Reff et al. |
| 6,455,315 B1 | 9/2002 | Baszczynski et al. |
| 6,458,594 B1 | 10/2002 | Baszczynski et al. |
| 6,541,231 B1 | 4/2003 | Baszczynski et al. |
| 6,552,248 B1 | 4/2003 | Bowen et al. |
| 6,573,425 B1 | 6/2003 | Baszczynski et al. |
| 6,624,297 B1 | 9/2003 | Baszczynski et al. |
| 6,630,322 B1 | 10/2003 | Perricaudet et al. |
| 6,632,980 B1 | 10/2003 | Yadav et al. |
| 6,664,108 B1 | 12/2003 | Baszczynski et al. |
| 6,759,571 B1 | 7/2004 | Robertson |
| 6,767,735 B1 | 7/2004 | Sugita et al. |
| 2001/0056583 A1 | 12/2001 | McElroy et al. |
| 2002/0023278 A1 | 2/2002 | Lyznik et al. |
| 2003/0226160 A1 | 12/2003 | Baszczynski et al. |
| 2003/0226164 A1 | 12/2003 | Suttle et al. |
| 2004/0101880 A1* | 5/2004 | Rozwadowski et al. ........ 435/6 |

FOREIGN PATENT DOCUMENTS

| | | |
|---|---|---|
| WO | WO9317116 | 9/1993 |
| WO | WO9747757 | 12/1997 |
| WO | WO9747758 | 12/1997 |
| WO | WO9840510 | 9/1998 |
| WO | WO9925821 | 5/1999 |
| WO | WO0012734 | 3/2000 |
| WO | WO0075289 | 12/2000 |
| WO | WO0111020 | 2/2001 |
| WO | WO0166717 | 9/2001 |
| WO | WO 0171019 | 9/2001 |
| WO | WO 0200875 | 1/2002 |
| WO | WO 0229071 | 4/2002 |
| WO | WO 02062986 | 8/2002 |
| WO | WO 02077246 | 10/2002 |

OTHER PUBLICATIONS

Albert et al., Site-specific integration of DNA into wild-type and mutant lox sites placed in the plant genome, Plant J. 7(4):649-659 (1995).
Bakkeren et al., Recovery of Agrobacterium tumefaciens T-DNA Molecules from Whole Plants Early after Transfer, Cell 57:847-857 (1989).
De Buck et al., The DNA sequences of T-DNA junctions suggest that complex T-DNA loci are formed by a recombination process resembling T-DNA integration, Plant J. 20(3):295-304 (1999).
Gallego et al., Positive-negative selection and T-DNA stability in Arabidopsis transformation, Plant Mol. Biol. 39:83-93 (1999).
Gutierrez, Geminiviruses and the plant cell cycle, Plant Mol. Biol. 43:763-772 (2000).
Halfter et al., Gene targeting in Arabidopsis thaliana, Mol. Gen. Genet. 231:186-193 (1992).
Hatada et al., Gene correction in hematopoietic progenitor cells by homologous recombination, Proc. Natl. Acad. Sci. USA 97(25):13807-13811 (2000).
Hormuzdi et al., A Gene-Targeting Approach Identifies a Function for the First Intron In Espression of the −1(1) Collagen Gene, Mol. Cell. Biol. 18(6):3368-3375 (1998).
Hrouda et al., High fidelity extrachromosomal recombination and gene targeting in plants. Mol. Gen. Genet. 243:106-111 (1994).
Jeske et al., DNA forms indicate rolling circle and recombination-dependent replication of Abutiton mosaic virus EMBO J 20(21):6158-6167 (2001).

(Continued)

*Primary Examiner*—David T Fox

(57) ABSTRACT

The invention provides novel methods of gene targeting using replication in order to increase the efficiency of targeted genetic modification in an eukaryotic organism. Included are vectors, expression cassettes, and modified cells, plants and seeds.

10 Claims, No Drawings

OTHER PUBLICATIONS

Keller et al., Efficient Gap Repair in Drosophila melanogaster Requires a Maximum of 31 Nucleotides of Homologous Sequence at the Searching Ends, Mol. Cell. Biol. 17(2):627-634 (1997).
Kempin et al., Targeted disruption in Arabidopsis, Nature 389:802-803 (1997).
Koller et al., Toward an animal model of cystic fibrosis: Targeted interruption of exon 10 of the cystic fibrosis transmembrane regulator gene in embryonic stem cells, Proc. Natl. Acad. Sci. USA 88:10730-10734 (1991).
Koukolikova-Nicola et al., Involvement of circular intermediates in the transfer of T-DNA from Agrobacterium tumefaciens to plant cells, Nature 313:191-196 (1985).
Lee et al., Homologous Recombination in Plant Cells after Agrobacterium-Mediated Transformation, Plant Cell 2:415-425 (1990).
Lyznik et al., Site-specific recombination for genetic engineering in plants, Plant Cell Rep. 21:925-932 (2003).
Machida et al., Plant-inducible recombination between the 25 bp border sequences of T-DNA in Agrobacterium tumefaciens, Mol. Gen. Genet. 204:374-382 (1986).
Miao et al., Targeted disruption of the TGA3 locus in Arabidopsis thaliana, Plant J. 7(2):359-365 (1995).
Miller et al., Targeted integration of the Ren-1D locus in mouse embryonic stem cells, Proc. Natl. Acad. Sci. USA 89:5020-5024 (1992).
Nassif et al., DNA homology requirements for mitotic gap repair in Drosophila, Proc. Natl. Acad. Sci. USA 90:1262-1266 (1993).
Noskov et al., Defining the minimal length of sequence homology required for selective gene isolation by TAR cloning, Nuc. Acids. Res. 29(6)e32:1-6 (2001).
Noskov et al., A genetic system for direct selection of gene-positive clones during recombinational cloning in yeast, Nuc. Acids Res. 30(2)e8:1-7 (2002).
Offringa et al., Extrachromosomal homologous recombintion and gene targeting in plant cells after Agrobacterium mediated transformation, EMBO J. 9(10):3077-3084 (1990).
Offringa et al., Nonreciprocal homologous recombination between Agrobacterium transferred DNA and a plant chromosomal locus, Proc. Natl. Acad. Sci. USA 90:7346-7350 (1993).
Osborne et al., A system for insertional mutagenesis and chromosomal rearrangement using the Ds transposon and Cre-lox, Plant J. 7(4)687-701 (1995).
Paszkowski et al., Gene targeting in plants, EMBO J. 7(13):4021-4026 (1988).
Puchta, Repair of genomic double-strand breaks in somatic plant cells by one-sided invasion of homologous sequences, Plant J. 13(3):331-339 (1998).
Reiss et al., RecA protein stimulates homologous recombination in plants, Proc. Natl. Acad. Sci. USA 93:3094-3098 (1996).
Riele et al., Highly efficient gene targeting in embryonic stem cells though homologous recombination with isogenic DNA constructs. Proc. Natl. Acad. Sci. USA 89:5128-5132 (1992).
Risseeuw et al., Targeted recombination in plants using Agrobacterium coincides with additional rearrangements at the target locus, Plant J. 7(1):109-119 (1995).
Salomon et al., Capture of genomic and T-DNA sequences during double-strand break repair in somatic plant cells, EMBO J. 17(20):6086-6095 (1998).
Rong et al., A Targeted Gene Knockout in Drosophila, Genetics 157:1307-1312 (2001).
Shesely et al., Correction of a human s-globin gene by gene targeting, Proc. Natl. Acad. Sci. USA 88:4294-4298 (1991).
Shinohara et al., Rad51/RecA protein families and the associated proteins in eukaryotes, Mutation Research 435:13-21 (1999).
Terada et al., Efficient gene targeting by homologous recombination in rice, Nature Biotechnology 20:1030-1034 (2002).
Thykjaer et al., Gene targeting approaches using positive-negative selection and large flanking regions, Plant Mol. Biol. 35:523-530 (1997).
Van Sloun et al., Determination of spontaneous loss of heterozygosity mutations in Aprt heterozygous mice, Nuc. Acids Res. 26(21):4888-4894 (1998).
Vergunst et al., Cre/lox-mediated site-specific integration of Agrobacterium T-DNA in Arabidopsis thaliana by transient expression of cre, Plant Mol. Biol. 38:393-406 (1998).
Vergunst et al., Site-specific integration of Agrobacterium T-DNA in Arabidopsis thaliana mediated by Cre recombinase, Nuc. Acids Res. 26(11):2729-2734 (1998).
Waters, Conjugation between bacterial and mammalian cells, Nature Genetics 29:375-376 (2001).
Zhao et al., T-DNA recombination and replication in maize cells, Plant J. 33:149-159 (2003).
Shen, et al., Excision of a transposable element from a viral vector introduced into maize plants by agroinfection, Plant J. (1992) 2(1):35-42.
Hoffman, et al., A specific member of the Cab multigene family can be efficiently targeted and disrupted in the moss *Physcomitrella patens*, Mol Gen Genet 261:92-99, (1999).

* cited by examiner

GENE TARGETING USING REPLICATING DNA MOLECULES

CROSS-REFERENCE TO RELATED APPLICATIONS

This application is a divisional of U.S. application Ser. No. 10/138,546, filed May 3, 2002, now U.S. Pat. No. 7,164,056, which is incorporated in its entirety by reference herein.

TECHNICAL FIELD

The present invention relates generally to plant molecular biology.

SUMMARY OF THE INVENTION

The present invention provides novel methods and compositions for carrying out gene targeting. The method uses homologous recombination processes endogenous in the cells of all organisms. Any gene of any organism can be modified by the methods of the invention as long as the sequence of at least a portion of the gene is known, or a DNA clone is available.

The invention provides methods for increasing gene targeting frequencies comprising introducing into a target cell a targeting vector comprising an origin of replication and further comprising a target modifying sequence which is compatible with a target site in the genome of the target cell. The target modifying sequence comprises the sequence modifications to be introduced into the target site sequence. A replicase is also provided in the target cell. Replication of the targeting vector stimulates homologous recombination between the targeting vector and the target site resulting in a gene targeting event.

In another embodiment, the invention provides methods for increasing gene targeting frequencies comprising introducing into a target cell a targeting vector comprising a transposon comprising an origin of replication and further comprising a target modifying sequence which is compatible with a target site in the genome of the target cell. A transposase is provided in the target cell, wherein the transposase is capable of excising the transposon to produce a replication-competent targeting vector. A replicase is also provided in the target cell. Replication of the targeting vector stimulates homologous recombination between the targeting vector and the target site resulting in a gene targeting event.

In another embodiment the invention provides methods for increasing gene targeting frequencies comprising introducing into a target cell a targeting vector comprising an origin of replication and further comprising a target modifying sequence which is compatible with a target site in the genome of the target cell, wherein the origin of replication and the target modifying sequence are flanked by site-specific recombination sites. A site-specific recombinase capable of excising the targeting vector to produce a replication-competent targeting vector is provided. A replicase is also provided in the target cell. Replication of the targeting vector stimulates homologous recombination between the targeting vector and the target site resulting in a gene targeting event.

The invention also provides cells and organisms produced by the methods. These cells or organisms comprise a modified target polynucleotide sequence produced by a method of the invention. The invention further provides progeny or seed produced by the modified cells or organisms, wherein the progeny or seed have inherited the gene targeted modification. The invention also provides isolated nucleic acids such as targeting vectors.

The compositions used in the invention comprise nucleic acids, such as targeting vectors, and expression cassettes. The compositions further comprise donor organisms comprising an integrated targeting vector, and target organisms comprising modified target sequences, and the progeny of each.

DETAILED DESCRIPTION OF THE INVENTION

Definitions

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "polypeptide" and "protein" are used interchangeably and mean proteins, protein fragments, modified proteins, amino acid sequences and synthetic amino acid sequences. The polypeptide can be glycosylated or not.

As used here, "polynucleotide" and "nucleic acid" are used interchangeably. A polynucleotide can be full-length or a fragment and includes polynucleotides that have been modified for stability. Unless otherwise indicated, the term includes reference to a specific sequence or its complement.

As used herein, "functional variant" or "functional derivative" or "functional fragment" are used interchangeably. As applied to polypeptides, the functional variant or derivative is a fragment, a modified polypeptide, or a synthetic polypeptide that provides a functional activity in a manner similar to the wild type, or naturally occurring, gene products As used herein, "origin of replication" refers to a polynucleotide region where DNA replication is initiated. The origin of replication is intended to include functional fragments, modifications, variants, and derivatives which retain the functional activity. Replication is usually initiated at the origin of replication by a replicase polypeptide.

As used herein, "replicase", or "replicase polypeptide" refers to polypeptides capable of stimulating DNA synthesis. The polynucleotides and polypeptides are intended to include functional variants, fragments, and derivatives which retain the functional activity. The polypeptides include proteins commonly referred to as "replication proteins", "replication associated proteins", or "replication initiation proteins". The polypeptide includes proteins in which all the "replication associated" or "replication" functions are encoded as a single protein, and those in which these functions are carried out by more than one protein, irrespective of whether proper or "inappropriate" splicing has occurred prior to translation.

As used herein, "replicase polynucleotide" refers to polynucleotides coding for a replicase polypeptide, including functional variants, derivatives, fragments, or functional homologs of characterized replicase polynucleotides. Replicase polynucleotides, functional variants and/or functional homologs from any organism can be used in the methods of the invention as long as the expressed replicase polypeptides bind to the origin of replication, and/or stimulate DNA replication.

As used herein, "plant" includes but is not limited to whole plants, plant parts, plant cells, plant tissue, and plant seeds.

As used herein, "site-specific recombinase" refers to any enzyme capable of being functionally expressed that catalyzes conservative site-specific recombination between its corresponding site-specific recombination sites. The site-specific recombinase may be naturally occurring, or a recombinantly produced polypeptide, fragment, variant, or derivative thereof that retains the activity of the naturally occurring recombinase.

As used herein "gene targeting" refers to a process whereby a specific sequence modification is facilitated at a desired genetic locus by a transforming nucleic acid, such as a targeting vector. Typically, the gene at the target locus is modified, removed, replaced or duplicated by the transforming nucleic acid. Modifications include at least one insertion, deletion, or substitution of one or more nucleotides at a target site.

As used herein "homologous recombination" refers to the process by which a recombination event occurs between two homologous nucleic acid regions.

As used herein "transposon" refers to a DNA sequence capable of moving from one place in the genome to another. Transposons are typically characterized by being flanked by terminal inverted repeat sequences required for transposition.

As used herein "transposase" refers to a polypeptide that mediates transposition of a transposon from one location in the genome to another. Transposases typically function to excise the transposon, and to recognize subterminal repeats and bring together the ends of the excised transposon, in some systems other proteins are also required to bring together the ends during transposition.

As used herein "targeting vector" refers to a nucleic acid comprising at least an origin of replication and a target modifying polynucleotide, wherein the target modifying polynucleotide comprises a modified version of the target sequence, containing any sequence modification to be introduced at the target site resulted in a desired genetic change at the target. The targeting vector can be integrated in a host genome and later excised to produce a gene targeting event. The targeting vector can be provided by any transformation method or introduced by sexual crossing.

As used herein "target polynucleotide" or "target site" refers to a polynucleotide sequence to be modified in the host organism. The target polynucleotide can be either an endogenous polynucleotide, or an exogenous polynucleotide previously introduced into the host organism. The target sequence may be any polynucleotide sequence, including but not limited to a polypeptide coding region. The target sequence may be a non-coding region, for example, a promoter, an intron, a terminator, an enhancer, or any other regulatory, structural polynucleotide, or other polynucleotide region.

As used herein "target modifying polynucleotide" refers to a polynucleotide comprising the sequence modification to be incorporated at the target site, wherein the sequence modification comprises at least one base pair difference as compared to the target site sequence. Sequence modifications to the target polynucleotide may include nucleotide substitutions, nucleotide or polynucleotide deletions, and/or nucleotide or polynucleotide insertions.

As used herein "donor organism" or "donor cell" refers to an organism, or cell, which comprises at least one of the following: a targeting vector, a replicase expression cassette, a recombinase expression cassette, and/or a transposase expression cassette, such that those components contained can be delivered to a target host organism in a heritable manner. For example, the component(s) may be delivered by sexually crossing the target host to the donor organism.

As used herein "target organism", "target cell", "host organism", or "host cell" refers to an organism, or cell, which comprises at least one target polynucleotide to be modified. Any one of the following: a targeting vector, a target modifying polynucleotide, a replicase expression cassette, a recombinase expression cassette, and/or a transposase expression cassette, may be introduced by any means including transient or stable transformation, sexually crossing to a donor, or fusion to a donor cell.

As used herein "expression cassette" refers to a nucleic acid construct, generated recombinantly or synthetically, with a series of specified nucleic acid elements which permit transcription of a particular nucleic acid in a host cell. The expression cassette can be incorporated into a plasmid, chromosome, mitochondrial DNA, plastid DNA, virus, or nucleic acid fragment. Typically, the expression cassette portion of an expression vector includes, among other sequences, a nucleic acid to be transcribed, and a promoter.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

In general, the invention provides a method for gene targeting in an organism by providing a targeting vector comprising a target modifying polynucleotide and an origin of replication, and providing replicase activity such that targeted sequence modifications are incorporated at the target site in the host genome. The target site can be any polynucleotide region, including but not limited to polypeptide coding regions, introns, exons, untranslated regions (UTR's), promoters, enhancers, terminators, or other regulators of gene expression, or any other region of interest. The targeting vector comprises at least an origin of replication and a target modifying polynucleotide. The target modifying polynucleotide shares sufficient homology with the target site so that homologous recombination can occur between the two polynucleotides. The target modifying polynucleotide has at least one base pair difference as compared to the target site, this base pair difference can comprise a point mutation (base change), insertion, or deletion. When replicase activity is provided, the frequency of incorporation of the sequence modifications at the target site is enhanced. The target site modification includes any changes which could suppress gene expression, such as the introduction of a premature stop codon, frameshift mutation, or changes to a promoter or other UTR, and the like. The changes also include modifications to increase gene expression or protein activity such as alterations to codons, or alterations to UTR's and the like. The targeting vector need not be integrated into the host genome, but may be maintained as an autonomously replicating vector. The targeting vector need not be circular in order to replicate, as illustrated by the work of Jeske et al. (2001) *EMBO* 20:6158-6167. The targeting vector may be introduced by any method, depending on the organism, including *Agrobacterium*-mediated transformation, biolistic methods, direct DNA delivery methods including microinjection, chemical methods, electroporation and the like.

The targeting vector may further comprise a replicase expression cassette wherein a replicase polynucleotide is operably linked to a promoter and other regulatory elements needed for expression of a replicase polypeptide. The promoter can be constitutive, inducible, or under developmental control as needed in order to regulate the expression of the replicase polypeptide.

If the targeting vector is incorporated into the genome, a method of excision can be used to release the targeting vector. The targeting vector may comprise flanking sequences for excision using systems such as site-specific recombinases, or transposases. The recombinase or transposase activity may be introduced using a recombinant expression cassette wherein the recombinase or transposase is operably linked to a promoter and other regulatory elements needed for expression of the polypeptide. The recombinase or transposase activity may also be provided by crossing a donor organism, which comprises a recombinase or transposase expression cassette, with a target organism comprising the integrated targeting vector. Methods of providing the transposase by crossing organisms are disclosed in WO 01/71019, the contents of which are herein incorporated by reference.

Replication

Examples of replication systems suitable for this invention include bacterial origins of replication and replication proteins, viral origins of replication and replication proteins, and eukaryotic replication systems.

Examples of suitable viral replication systems include abutilon mosaic virus (AbMV), African cassava mosaic virus (ACMV), banana streak virus (BSV), bean dwarf mosaic virus (BDMV), bean golden mosaic virus (BGMV), beet curly top virus (BCTV), beet western yellow virus (BWYV), and other luteoviruses, cassava latent virus (CLV), carnation etched ring virus (CERV), cauliflower mosaic virus (CaMV), chloris striate mosaic virus (CSMV), commelina yellow mottle virus (CoYMV), cucumber mosaic virus (CMV), dahlia mosaic virus (DMV), digitaria streak virus (DSV), figwort mosaic virus (FMV), hop stunt viroid (HSV), maize streak virus (MSV), mirabilias mosaic virus (MMV), miscanthus streak virus (MiSV), potato stunt tuber virus (PSTV), panicum streak virus (PSV), potato yellow mosaic virus (PYMV), rice tungro bacilliform virus (RTBV), soybean chlorotic mottle virus (SoyCMV), squash leaf curl virus (SqLCV), strawberry vein banding virus (SVBV), sugarcane streak virus (SSV), thistle mottle virus (ThMV), tobacco mosaic virus (TMV), tomato golden mosaic virus (TGMV), tomato mottle virus (TmoV), tobacco ringspot virus (TobRV), tobacco yellow dwarf virus (TobYDV), tomato leaf curl virus (TLCV), tomato yellow leaf curl virus (TYLCV), tomato yellow leaf curl virus-Thailand (TYLCV-t), wheat dwarf virus (WDV), and the bean yellow dwarf virus (BYDV). Other plant viruses with DNA replicases suitable for use in the invention include members of the nanovirus group such as banana bunchy top virus (BBTV), milk vetch dwarf virus (MDV), subterranean clover stunt virus (SCSV), and Ageratum yellow vein virus (AYVV).

Other virus systems include the papova viruses such as SV40, polyoma viruses, adenoviruses, papillomaviruses such as human papillomavirus (HPV) and bovine papillomavirus (BPV), herpes viruses such as herpes simplex virus (HSV), cytomegalovirus (CMV), and Epstein-Barr virus (EBV), and retroviruses such as human immunodeficiency virus (HIV), human T lymphotropic virus (HTVL), simian immunodeficiency virus (SIV), simian sarcoma virus (SSV), Rous sarcoma virus (RSV), caprine arthritis-encephalitis virus (CAEV), murine leukemia virus (MLV), avian leukemia virus (ALV), bovine leukemia virus (BLV), feline immunodeficiency virus (FIV), equine infectious anemia virus (EIAV), and endogenous retrovirus (ERV), or a baculovirus system. For example, a viral vector system for use in animal cells is disclosed in WO 99/09139, and herein incorporated by reference.

Excision of Integrated Targeting Vectors

The targeting vector, flanked by site-specific recombination sites and/or transposon sequences, may be randomly integrated in the genome of a donor or target organism. Gene targeting can be activated by excising the target vector, which is then capable of replication and homologous recombination with the target sequence. The integrated vector may be excised by providing site-specific recombinase or a transposase activity. Any system or method to excise the integrated targeting vector can be used in the invention.

Examples of transposons and transposases suitable for this invention include the P element transposon from *Drosophila* (Gloor, G. B. et al. (1991) *Science* 253:1110-1117), the Copia, Mariner and Minos elements from *Drosophila*, the Hermes elements from the housefly, the PiggyBack elements from *Trichplusia ni*, Tc1 elements from *C. elegans*, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), IAP elements from mice (retrotransposon), and the like. A transposable element system effective in vertebrates and invertebrates is a synthetic SB transposon system derived from Tc1/mariner disclosed in WO 98/40510, the contents of which is herein incorporated by reference.

Site-specific recombination systems are reviewed in Sauer (1994) *Current Opinion in Biotechnology* 5:521-527, Nunes-Duby et al. (1998) *Nucl. Acids Res.* 26:391-406, and Sadowski (1993) *FASEB* 7:760-767, the contents of which are herein incorporated by reference. Any site-specific recombination can be used in the invention. Examples of site-specific recombination systems suitable for this invention include the integrase family, such as the FLP/FRT system from yeast, and the Cre/Lox system from bacteriophage P1, as well as the Int, and R systems. The resolvase family can also be used, for example γδ resolvase, and the like. Examples of site-specific recombination systems used in plants can be found in U.S. Pat. No. 5,929,301; U.S. Pat. No. 6,175,056; WO 99/25821; U.S. Pat. No. 6,331,661; WO 99/25855; WO 99/25841, and WO 99/25840, the contents of each are herein incorporated by reference.

Markers

Gene targeting can be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Markers useful in the invention include positive and negative selectable markers as well as markers that facilitate screening, such as visual markers. Selectable markers include genes carrying resistance to an antibiotic such as spectinomycin (e.g. the aada gene, Svab et al. 1990 *Plant Mol. Biol.* 14:197), streptomycin (e.g., aada, or SPT, Svab et al. 1990 *Plant Mol. Biol.* 14:197; Jones et al. 1987 *Mol. Gen. Genet.* 210:86), kanamycin (e.g., nptII, Fraley et al. 1983 *PNAS* 80:4803), hygromycin (e.g., HPT, Vanden Elzen et al. 1985 *Plant Mol. Biol.* 5:299), gentamycin (Hayford et al. 1988 *Plant Physiol.* 86:1216), phleomycin, zeocin, or bleomycin (Hille et al. 1986 *Plant Mol. Biol.* 7:171), or resistance to a herbicide such as phosphinothricin (bar gene), or sulfonylurea (acetolactate synthase (ALS)) (Charest et al. (1990) *Plant Cell Rep.* 8:643), genes that fulfill a growth requirement on an incomplete media such as HIS3, LEU2, URA3, LYS2, and TRP1 genes in yeast, and other such genes known in the art. Negative selectable markers include cytosine deaminase (codA) (Stougaard 1993 *Plant J.* 3:755-761), tms2 (DePicker et al. 1988 *Plant Cell Rep.* 7:63-66), nitrate reductase (Nussame et al. 1991 *Plant J.* 1:267-274), SU1 (O'Keefe et al. 1994 *Plant Physiol.* 105:473-482), aux-2 from the Ti plasmid of *Agrobacterium*, and thymidine kinase. Screenable markers include fluorescent proteins such as green fluorescent protein (GFP) (Chalfie et al., 1994 *Science* 263:802; U.S. Pat. No. 6,146,826; U.S. Pat. No. 5,491,084; and WO 97/41228), reporter enzymes such as β-glucuronidase (GUS) (Jefferson R. A. 1987 *Plant Mol. Biol. Rep.* 5:387; U.S. Pat. No. 5,599,670; and U.S. Pat. No. 5,432,081), β-galactosidase (lacZ), alkaline phosphatase (AP), glutathione S-transferase (GST) and luciferase (U.S. Pat. No. 5,674,713; and Ow et al. 1986 *Science* 234(4778): 856-859), visual markers like anthocyanins such as CRC (Ludwig et al. (1990) *Science* 247(4841):449-450) R gene family (e.g. Lc, P, S), A, C, R-nj, body and/or eye color genes in *Drosophila*, coat color genes in mammalian systems, and others known in the art.

One or more markers may be used in order to select and screen for gene targeting events. One common strategy for gene disruption involves using a target modifying polynucleotide in which the target is disrupted by a promoterless selectable marker. Since the selectable marker lacks a promoter, random integration events are unlikely to lead to transcription of the gene. Gene targeting events will put the selectable marker under control of the promoter for the target gene. Gene targeting events are identified by selection for expression of the selectable marker. Another common strategy utilizes a positive-negative selection scheme. This scheme utilizes two selectable markers, one that confers resistance ($R^+$) coupled with one that confers a sensitivity ($S^+$), each with a promoter. When this polynucleotide is randomly inserted, the resulting phenotype is $R^+/S^+$. When a gene targeting event is generated, the two markers are uncoupled and the resulting phenotype is $R^+/S^-$. Examples of using positive-negative selection are found in Thykjaer et al. (1997) *Plant Mol. Biol.* 35:523-530; and WO 01/66717, which are herein incorporated by reference.

Target Sequences

The methods of the invention can be practiced in any organism in which a method of transformation is available, and for which there is at least some sequence information for the target sequence of interest, or for a region flanking the target sequence of interest. It is also understood that two or more sequences could be targeted by sequential transformation, co-transformation with more than one targeting vector, or the construction of a targeting vector comprising more than one target modifying sequence.

The target sequences can be selected from any portion of a genome of interest. Typically, targets comprise genes or regulatory regions, although regions adjacent to or near genes may be selected such that modifications may be made without disrupting gene expression.

General categories of target sequences of interest include, for example, those genes involved in information, such as zinc fingers, those involved in communication, such as kinases, and those involved in housekeeping, such as heat shock proteins.

Target sequences further include coding regions and non-coding regions such as promoters, enhancers, terminators, introns and the like, which may be modified in order to alter the expression of a gene of interest. For example, an intron sequence can be added to the 5' region to increase the amount of mature message that accumulates (see for example Buchman and Berg, *Mol. Cell Biol.* 8:4395-4405 (1988); and Callis et al., *Genes Dev.* 1:1183-1200 (1987)).

The target sequence may be an endogenous sequence, or may be an introduced exogenous sequence, or transgene. For example, this method may be used to alter the regulation or expression of a transgene, or to remove a transgene or other introduced sequence such as an introduced site-specific recombination site. A sequence of interest could also be introduced at a target site, for example a site-specific recombination site could be introduced, a endonuclease restriction site could be introduced, a polynucleotide tag could be introduced, or a protein purification tag such as that encoding hexa-histidine could be inserted to facilitate purification of a expressed protein of interest.

In plants, more specific categories of target sequences include genes encoding agronomic traits, insect resistance, disease resistance, herbicide resistance, sterility, grain characteristics, and commercial products. Genes of interest also included those involved in oil, starch, carbohydrate, or nutrient metabolism as well as those affecting, for example, kernel size, sucrose loading, and the like. The quality of grain is reflected in traits such as levels and types of oils, saturated and unsaturated, quality and quantity of essential amino acids, and levels of cellulose.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations). Glyphosate tolerance can be obtained form the EPSPS gene.

Sterility genes can also be targeted, including male tissue-preferred genes and genes with male sterility phenotypes such as QM, described in U.S. Pat. No. 5,583,210. Other genes include kinases and those encoding compounds toxic to either male or female gametophytes.

For example, in *Arabidopsis*, the TGA3 locus was knocked out by disrupting the gene with a kanamycin-resistance cassette (Maio and Lam (1995) *Plant J.* 7:359-365). The targeting cassette had about 4 kb of homology to the 5' end of TGA3 and about 3 kb of homology to the 3' end of the gene. In another report, the AGL5 MADS-box gene has been knocked out by homologous recombination in *Arabidopsis* (Kempin et al. 1997 *Nature* 389:802-803). The targeting construct consisted of a kanamycin-resistance cassette inserted into the AGL5 sequence roughly 3 kb from the 5' end and 2 kb from the 3' end.

In animals, more specific categories of target sequences include genes involved in various diseases or medical conditions, such as cancer, including targets such as tumor suppressor genes (e.g., p53, p73, p51, or p40) and oncogenes (e.g., c-myc, c-jn, c-fos, c-rel, c-qin, c-neu, c-src, c-abl, c-lck, c-mil/raf, c-ras, c-sis, or c-fps); obesity, fertility, diabetes, hypertension, coronary disease, neurological disorders, cystic fibrosis, multiple sclerosis, muscular dystrophy, genetic disorders, and the like.

Target Modifying Sequences, Homologous Recombination, and Gene Targeting

Homologous recombination is recombination occurring as a result of interaction between segments of genetic material that is homologous over a sufficient length of nucleotide sequence. Homologous recombination is an enzyme-catalyzed process that occurs in essentially all cell types. The reaction takes place when nucleotide strands of homologous sequence are aligned in proximity to one another, and entails breaking phosphodiester bonds in the nucleotide strands and rejoining with neighboring homologous strands or with an homologous sequence on the same strand. The breaking and rejoining can occur with precision, such that the sequence fidelity is retained.

The frequency of homologous recombination is influenced by a number of factors. Different organisms vary with respect to the amount of homologous recombination that occurs in their cells and the relative proportion of homologous to non-homologous recombination that occurs is also species-variable. Generally, the length of the region of homology affects the frequency of homologous recombination events, the longer the region of homology, the greater the frequency. The length of the homology region needed to observe homologous recombination is also species-variable. In many cases, at least 5 kb of homology has been utilized, but homologous recombination has been observed with as little as 25-50 bp of homology. The minimum length of homology needed has been estimated at 20-50 bp in *E. coli* (Singer et al. (1982) *Cell* 31:25-33; Shen & Huang (1986) *Genetics* 112:441-457; Watt et al. (1985) *PNAS* 82:4768-4772), 63-89 bp in *S. cerevisaie* (Sugawara & Haber (1992) *Mol. Cell. Biol.* 12:563-575), and 163-300 bp in mammalian cells (Rubnitz & Subramani (1984) *Mol. Cell. Biol.* 4:2253-2258; Ayares et al. (1986) *PNAS* 83:5199-5203; Liskay et al. (1987) *Genetics* 115:161-167).

However, differences in the frequency of homologous recombination can be offset somewhat by sensitive selection for recombinations that do occur. Other factors, such as the degree of homology between the donor (target modifying polynucleotide) and target sequence will also influence the frequency of homologous recombination events, as is well-understood in the art. In ES cells, Te Riele et al. observed that use of targeting constructs based on isogenic DNA resulted in a 20-fold increase in targeting efficiency (Te Riele et al. (1992) *PNAS* 89:5128-5132). They concluded that base sequence divergence between non-isogenic DNA sources was the major influence on homologous recombination efficiency. Absolute limits for the length of homology or the degree of homology cannot be fixed, but depend on the number of events that can be generated, screened, and selected. All such factors are well known in the art, and can be taken into account when using the invention for gene targeting in any given organism.

Gene targeting has been demonstrated in insects. In *Drosophila*, Dray and Gloor found that as little as 3 kb of total template:target homology sufficed to copy a large non-homologous segment of DNA into the target with reasonable efficiency. (*Genetics* 147:689-699 1997). Using FLP-mediated DNA integration at a target FRT in *Drosophila*, Golic (Golic et al. (1997) *Nucl. Acids Res.* 25:3665) showed integration was approximately 10-fold more efficient when the donor and target shared 4.1 kb of homology compared to 1.1 kb of homology. Therefore, data from *Drosophila* indicates that 2-4 kb of homology is sufficient for efficient targeting, but there is some evidence that much less homology may suffice, on the order of about 30 bp to about 100 bp (Nassif & Engels (1993) *PNAS* 90:1262-1266; Keeler & Gloor (1997) *Mol. Cell Biol.* 17:627-634).

Gene targeting has been demonstrated in plants. The parameters for gene targeting in plants have primarily been investigated by rescuing introduced truncated selectable marker genes. In these experiments, the homologous DNA fragments for homologous recombination were typically between 0.3 kb to 2 kb. Observed frequencies for homologous recombination were on the order of $10^{-3}$-$10^{-5}$. See, for example, Halfter et al. (1992) *Mol. Gen. Genet.* 231:186-193; Offringa et al. (1990) *EMBO* 9:3077-3084; Offringa et al. (1993) *PNAS* 90:7346-7350; Paszkowski et al. (1988) *EMBO* 7:4021-4026; Hourda and Paszkowski (1994) *Mol. Gen. Genet.* 243:106-111; and Risseeuw et al. (1995) *Plant J.* 7:109-119.

An endogenous, non-selectable gene was targeted in *Arabidopsis*. The targeting vector contained a region of about 7 kb homologous to the target gene and the targeting frequency was estimated to be at least $3.9 \times 10^{-4}$ (Maio and Lam (1995) *Plant J.* 7:359-365).

Using a positive-negative selection scheme and a targeting vector containing up to 22.9 kb of sequence homologous to the target, Thykjaer and co-workers detected gene targeting with a frequency less than $5.3 \times 10^{-5}$, despite the large flanking sequences available for recombination (Thykjaer et al. (1997) *Plant Mol. Biol.* 35:523-530). In *Arabidopsis*, the AGL5 MADS-box gene was knocked out by homologous recombination (Kempin et al. (1997) *Nature* 389:802-803) using a targeting construct consisting of a kanamycin-resistance cassette inserted into the AGL5 sequence roughly 3 kb from the 5' end and 2 kb from the 3' end. Of the 750 kanamycin-resistant transgenic lines that were generated, one line contained the anticipated insertion.

Gene targeting has also been accomplished in other organisms. For example, at least 150-200 bp of homology was required for homologous recombination in the parasitic protozoan *Leishmania*, regions less than 1 kb a decrease in the length had a linear effect on the targeting frequency, and the targeting frequency plateaus at 1-2 kb of homology (Papadopoulou and Dumas (1997) *Nucl. Acids Res.* 25:4278-4286). In the filamentous fungus *Aspergillus nidulans*, gene replacement has been accomplished with as little as 50 bp flanking homology (Chaveroche et al. (2000) *Nucl. Acids Res.* 28(22): e97). Targeted gene replacement has also been demonstrated in the ciliate *Tetrahymena thermophila* (Gaertig et al. (1994) *Nucl. Acids Res.* 22:5391-5398).

In mammals, gene targeting has been most successful in the mouse as pluripotent embryonic stem cell lines exists (ES) that can be grown in culture, transformed, selected and introduced into an embryonic stage of a mouse embryo. Embryos bearing inserted transgenic ES cells develop as genetically chimeric offspring. By interbreeding siblings, homozygous mice carrying the selected genes can be obtained. An overview of the process is provided in Watson et al. (1992) Recombinant DNA, $2^{nd}$ Ed., Scientific American Books distributed by WH Freeman & Co.; Capecchi, M R (1989) *Trends in Genetics* 5:70-76; and Bronson, S K (1994) *J. Biol. Chem.* 269:27155-27158. Both homologous and non-homologous recombination occur in mammalian cells. While both processes occur with low frequency, non-homologous recombination occurs more frequently than homologous recombination. ES cells are transfected with a DNA construct that combines a donor DNA having the modification to be introduced at the target site combined with flanking sequence homologous to the target site, and marker genes as needed for selection, as well as any other desired sequences. The donor construct need not be integrated into the genome initially, but can recombine with the target site by homologous recombination, or become integrated by non-homologous recombination. Since homologous recombination events are rare, dual selection can be used to select for gene targeted events and to select against random integration. The selections are conveniently carried out in vitro on ES cells in culture. Other screening, such as PCR, can also be used to identify desired events. In general, the frequency of homologous recombination is increased as the length of the region of homology in the donor is increased, with at least 5 kb of homology commonly used. However, homologous recombination has been observed with as little as 25-50 bp of homology. It has been observed that small deletions or insertions into the target site are introduced with higher frequency than point mutations, but any desired modification can be obtained by appropriate design of donor vector, and selection and/or screening methods.

In an effort to create a mouse model system for cystic fibrosis Koller et al. used a targeting construct to disrupt exon 10 of the CTFR gene (Koller et al. (1991) *PNAS* 88:10730-10734). The construct shared homology to 7.8 kb of the target, spanning exon 10, and replaced part of the exon with two neo genes which causes a premature stop codon. A gene targeting frequency of $4 \times 10^{-4}$ was observed in ES cells.

In ES cells comprising two renin genes (Ren-1D and Ren-2) which share about 95% sequence identity at the genomic level, a targeting construct with about 5.5 kb of homology across exons 2-5 of Ren-1D specifically recombined only with the target gene with a gene targeting frequency of $5.29 \times 10^{-3}$. (Miller et al. (1992) *PNAS* 89:5020-5024). It was estimated that the targeting frequency observed was enhanced about 2.7-fold by the inclusion of a negative selectable marker in the targeting construct.

In order to study the transcriptional control of type I collagen, the first intron of CollA1 was targeted in mouse ES cells (Hormuzdi et al. (1998) *Mol. Cell. Biol.* 18:3368-3375). The targeting construct, which shared about 13 kb of homology to the target, resulted in a 1.3 kb deletion in intron 1. Even though there is a large deletion in the first intron, the study showed the intron was still correctly spliced.

A point mutation in β-globin causes sickle cell disease. Using a mouse-human hybrid cell line, BSM, which contains human chromosome 11, the sickle cell allele $β^S$-globin was corrected to the normal $β^A$-globin allele (Shesley et al. (1991) *PNAS* 88:4294-4298). The targeting vector comprised 4.7 kb of homology to the β-globin gene, as well as a selectable marker outside of the target gene, and resulted in a gene targeting frequency of at least $1 \times 10^{-4}$.

Gene targeting in mammals other than mouse has been limited by the lack of stem cells capable of being transplanted to oocytes or developing embryos. However, McCreath, K J et al. (2000) *Nature* 405:1066-1069 have reported successful gene targeting in sheep by transformation and selection in primary embryo fibroblast cells. The targeted fibroblast nuclei were transferred to enucleated egg cells followed by implantation in the uterus of a host mother. The technique yields a homozygous, non-chimeric offspring, however the time available for targeting and selection is short.

The organisms which can be used in the invention include, but are not limited to: insects, including *Coleoptera, Diptera*, such as *Drosophila, Hemiptera, Homoptera, Hymenoptera, Lepidoptera*, and *Orthoptera*; plants, including both monocotyledonous and dicotyledonous plants such as, but not limited to, maize, rice, wheat, oats, barley, sorghum, millet, soybean and other legumes, canola, *Brassica*, alfalfa, sunflower, safflower, *Arabidopsis*, cotton, potato, tomato, tobacco and the like; animals including mice, rats, sheep, pigs, bovines, amphibians, such as *Xenopus*, fish, such as zebrafish, birds; invertebrates such as *C. elegans*; fungi (Chaveroche et al. (2000) *Nucl. Acids Res.* 28(22):e97; DeLozane and Spudich (1987) *Science* 236:1086-1091); and protozoa such as ciliates (Gaertig et al. (1994) *Nucl. Acids Res.* 22:5891-5398), and/or parasitic protozoa (Papadopoulou and Dumas (1997) *Nucl. Acids Res.* 25:4278-4286), and the like.

The targeted event can be effected in the whole organism, or limited to certain tissue or cell types or even particular subcellular organelles. For example, homologous recombination has been used to target foreign genes into the plastid genome in tobacco (Zoubenko et al. (1994) *Nucl. Acids Res.* 22:3819-3824), and to correct a defective gene in hematopoietic progenitor cells (Hatada et al. (2000) *PNAS* 97:13807-13811).

The amount of homology shared between the target and the target modifying polynucleotide can vary and includes unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19, and 20 bp.

Nucleic Acids

Polynucleotides, including targeting vectors, target modifying polynucleotides, replicase polynucleotides, origins of replication, recombinase polynucleotides, transposon polynucleotides, transposase polynucleotides, selectable markers, and any other polynucleotides of interest, useful in the present invention can be obtained using (a) standard recombinant methods, (b) synthetic techniques, or combinations thereof. In general, examples of appropriate molecular biological techniques and instructions are found in Sambrook et al., *Molecular Cloning: A Laboratory Manual*, 2nd Ed., Cold Spring Harbor Laboratory, Vols. 1-3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997), all are herein incorporated by reference.

Polynucleotides and functional variants useful in the invention can be obtained using primers that selectively hybridize under stringent conditions. Primers are generally at least 12 bases in length and can be as high as 200 bases, but will generally be from 15 to 75, typically from 15 to 50. Functional fragments can be identified using a variety of techniques such as restriction analysis, Southern analysis, primer extension analysis, and DNA sequence analysis.

Variants of the nucleic acids can be obtained, for example, by oligonucleotide-directed mutagenesis, linker-scanning mutagenesis, mutagenesis using the polymerase chain reaction, and the like. See, for example, Ausubel, pages 8.0.3-8.5.9. Also, see generally, McPherson (ed.), *DIRECTED MUTAGENESIS: A Practical approach*, (IRL Press, 1991). Thus, the present invention also encompasses DNA molecules comprising nucleotide sequences that have substantial sequence similarity with the inventive sequences. Conservatively modified variants are preferred.

Nucleic acids produced by sequence shuffling of useful polynucleotides can also be used. Sequence shuffling is described in PCT publication No. 96/19256. See also, Zhang, J.-H., et al. *Proc. Natl. Acad. Sci. USA* 94:4504-4509 (1997).

Also useful are 5' and/or 3' UTR regions for modulation of translation of heterologous coding sequences. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short reading frames 5' of the appropriate AUG in the 5' UTR (Kozak, supra, Rao et al., *Mol. and Cell. Biol.* 8:284 (1988)).

Further, the polypeptide-encoding segments of the polynucleotides can be modified to alter codon usage. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387-395 (1984)) or MacVector 4.1 (Eastman Kodak Co., New Haven, Conn.).

For example, the polynucleotides can be optimized for enhanced or suppressed expression in the target organism. In the case of plants, see, for example, EPA0359472; WO91/16432; Perlak et al. (1991) *Proc. Natl. Acad. Sci. USA* 88:3324-3328; and Murray et al. (1989) *Nucleic Acids Res.* 17:477-498, the disclosures of which are incorporated herein by reference. In this manner, the genes can be synthesized utilizing species-preferred codons.

The nucleic acids may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

The polynucleotides can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The targeting vectors may comprise large regions of DNA with homology to the target site. Examples of construction of targeting vectors with large fragments of DNA are found in Lalioti and Heath (2001) *Nucl. Acids Res.* 29(3):e14; Akiyama et al. (2000) *Nucl. Acids Res.* 28(16):e77; and Angrand et al. (1999) *Nucl. Acids Res.* 27(17):e16. Transformation-associated recombination (TAR) cloning methods may also be used to isolate large regions of DNA. Examples of minimal homology required and selection of clones are found in Noskov et al. (2001) *Nucl. Acids Res.* 29(6):e32 and Noskov et al. (2002) *Nucl. Acids Res.* 30(2):e8.

To construct genomic libraries, large segments of genomic DNA are generated by random fragmentation. Examples of appropriate molecular biological techniques and instructions are found in Sambrook et al., *Molecular Cloning: A Laboratory Manual*, 2nd Ed., Cold Spring Harbor Laboratory, Vols. 1-3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The genomic library can be screened using a probe based upon the sequence of a nucleic acid used in the present invention. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The hybridization can be conducted under low stringency conditions which include hybridization with a buffer solution of 30% formamide, 1 M NaCl, 1% SDS (sodium dodecyl sulfate) at 37° C., and a wash in 1× to 2×SSC (20×SSC=3.0 M NaCl/0.3 M trisodium citrate) at 50° C. In another option, the hybridization can be conducted under moderate stringency conditions which include hybridization in 40% formamide, 1 M NaCl, 1% SDS at 37° C., and a wash in 0.5× to 1×SSC at 55° C. In yet another option, the hybridization can be conducted under high stringency conditions which include hybridization in 50% formamide, 1 M NaCl, 1% SDS at 37° C., and a wash in 0.1×SSC at 60° C.

An extensive guide to the hybridization of nucleic acids is found in Tijssen, *Laboratory Techniques in Biochemistry and Molecular Biology—Hybridization with Nucleic Acid Probes*, Part I, Chapter 2 "*Overview of principles of hybridization and the strategy of nucleic acid probe assays*", Elsevier, N.Y. (1993); and *Current Protocols in Molecular Biology*, Chapter 2, Ausubel et al., Eds., Greene Publishing and Wiley-Interscience, New York (1995). Often, cDNA libraries will be normalized to increase the representation of relatively rare cDNAs.

The nucleic acids can be amplified from nucleic acid samples using amplification techniques. For instance, polymerase chain reaction (PCR) technology can be used to amplify the sequences of polynucleotides of the present invention and related genes directly from genomic DNA or libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481-486 (1997).

The nucleic acids can also be prepared by direct chemical synthesis by methods such as the phosphotriester method of Narang et al., *Meth. Enzymol.* 68:90-99 (1979); the phosphodiester method of Brown et al., *Meth. Enzymol.* 68:109-151 (1979); the diethylphosphoramidite method of Beaucage et al., *Tetra. Lett.* 22:1859-1862 (1981); the solid phase phosphoramidite triester method described by Beaucage and Caruthers, *Tetra. Letts.* 22(20):1859-1862 (1981), e.g., using an automated synthesizer, e.g., as described in Needham-VanDevanter et al., *Nucleic Acids Res.*, 12:6159-6168 (1984); and, the solid support method of U.S. Pat. No. 4,458,066.

Expression cassettes comprising the isolated polynucleotide sequences of interest are also provided. An expression cassette will typically comprise a polynucleotide operably linked to transcriptional initiation regulatory sequences that will direct the transcription of the polynucleotide in the intended host cell, such as tissues of a transformed plant.

The construction of expression cassettes that can be employed in conjunction with the present invention is well known to those of skill in the art in light of the present disclosure. See, e.g., Sambrook et al. (1989) *Molecular Cloning: A Laboratory Manual* Cold Spring Harbor, N.Y.; Gelvin et al. (1990) *Plant Molecular Biology Manual*; Prakash et al. eds. (1993) *Plant Biotechnology: Commercial Prospects and Problems*, Oxford & IBH Publishing Co., New Delhi, India; and Heslot et al. (1992) *Molecular Biology and Genetic Engineering of Yeasts* CRC Press, Inc., USA; each incorporated herein in its entirety by reference.

For example, expression cassettes may include (1) a nucleic acid under the transcriptional control of 5' and 3' regulatory sequences and (2) a dominant selectable marker. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or even from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395-4405 (1988); Callis et al., *Genes Dev.* 1:1183-1200 (1987). Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the polynucleotide sequences useful in the present invention will typically comprise a marker gene that confers a selectable phenotype on plant cells. Usually, the selectable marker gene will encode antibiotic or herbicide resistance. Suitable genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorsulfuron.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253-277 (1987). Exemplary *A. tumefaciens* vectors useful herein are plasmids pKYLX6 and pKYLX7 of Schardl et al., *Gene*, 61:1-11 (1987) and Berger et al., *Proc. Natl. Acad. Sci. U.S.A.*, 86:8402-8406 (1989). Another useful vector herein is plasmid pB 101.2 that is available from Clontech Laboratories, Inc. (Palo Alto, Calif.). A variety of plant viruses that can be employed as vectors are known in the art and include cauliflower mosaic virus (CaMV), geminivirus, brome mosaic virus, and tobacco mosaic virus.

Useful polynucleotides can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Nat'l. Acad. Sci. (USA)* 85: 8805-8809 (1988); and Hiatt et al., U.S. Pat. No. 4,801,340.

Another method of suppression is sense suppression. For an example of the use of this method to modulate expression of endogenous genes see, Napoli et al., *The Plant Cell* 2: 279-289 (1990) and U.S. Pat. No. 5,034,323. Another method of down-regulation of the protein involves using PEST sequences that provide a target for degradation of the protein.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585-591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065-4076, describe covalent bonding of a single-stranded DNA fragment with alkylating derivatives of nucleotides complementary to target sequences. A report of similar work by the same group is that by Knorre, D. G., et al., *Biochimie* (1985) 67:785-789. Iverson and Dervan also showed sequence-specific cleavage of single-stranded DNA mediated by incorporation of a modified nucleotide which was capable of activating cleavage (*J Am Chem Soc* (1987) 109:1241-1243). Meyer, R. B., et al., *J Am Chem Soc* (1989) 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197-3203. Use of crosslinking in triple-helix forming probes was also disclosed by Home et al., *J Am Chem Soc* (1990) 112:2435-2437. Use of N4, N4-ethanocytosine as an alkylating agent to crosslink to single-stranded oligonucleotides has also been described by Webb and Matteucci, *J Am Chem Soc* (1986) 108:2764-2765; *Nucleic Acids Res* (1986) 14:7661-7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins useful in the present invention include proteins derived from the native protein by deletion (so-called truncation), addition or substitution of one or more amino acids at one or more sites in the native protein. In constructing variants of the proteins of interest, modifications will be made such that variants continue to possess the desired activity.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

The present invention includes catalytically active polypeptides (i.e., enzymes). Catalytically active polypeptides will generally have a specific activity of at least 20%, 30%, or 40%, or at least 50%, 60%, or 70%, or at least 80%, 90%, 95%, or 100% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; or at least 60%, 70%, 80%, 90%, 95% or 100%. Methods of assaying and quantifying measures of enzymatic activity and substrate specificity ($k_{cat}/K_m$), are well known to those of skill in the art.

The methods of the present invention can be used with any cell such as bacteria, yeast, insect, mammalian, or plant cells. The transformed cells produce viral replicase protein.

An intermediate host cell may be used in the practice of this invention to increase the copy number of the targeting vector, and/or replicase, recombinase, or transposase expression cassettes. With an increased copy number, the vector containing the nucleic acid of interest can be isolated in significant quantities for introduction into the desired target host cells. Intermediate host cells that can be used in the practice of this invention include prokaryotes, including bacterial hosts such as *Eschericia coli, Salmonella typhimurium*, and *Serratia marcescens*. Eukaryotic hosts such as yeast or filamentous fungi may also be used in this invention. One can use target host specific promoters that do not cause expression of the polypeptide in bacteria.

Commonly used prokaryotic control sequences include promoters such as the beta lactamase (penicillinase) and lactose (lac) promoter systems (Chang et al., *Nature* 198:1056 (1977)), the tryptophan (trp) promoter system (Goeddel et al., *Nucl. Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Expression systems for expressing a protein of the present invention are available using *Bacillus* sp. and *Salmonella* (Palva et al. (1983) *Gene* 22: 229-235; Mosbach et al. (1983) *Nature* 302: 543-545).

Synthesis of heterologous proteins in yeast is well known. See Sherman, F. et al. *Methods in Yeast Genetics*, Cold Spring Harbor Laboratory (1982). Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

The protein can be isolated from yeast by lysing the cells and applying standard protein isolation techniques to the lysates. The monitoring of the purification process can be accomplished by using Western blot techniques or radioimmunoassay of other standard immunoassay techniques.

The proteins useful in the present invention can also be constructed using non-cellular synthetic methods. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A*; Merrifield et al., *J. Am. Chem. Soc.* 85:2149-2156 (1963), and Stewart et al., *Solid Phase Peptide Synthesis, 2nd ed.*, Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicyclohexylcarbodiimide) are known to those of skill.

The proteins useful in this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. Detection of the expressed protein is achieved by methods known in the art, for example, radioimmunoassays, Western blotting techniques or immunoprecipitation.

In certain embodiments, the invention can be practiced in a wide range of plants such as monocots and dicots. For example, the methods of the present invention can be employed in corn, soybean, sunflower, safflower, potato, tomato, sorghum, canola, wheat, alfalfa, cotton, rice, barley and millet.

Transformation

The method of transformation/transfection is not critical to the invention; various methods of transformation or transfection are currently available. As newer methods are available to transform host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide useful in the present invention, for example a cDNA, RNA or a genomic sequence, will be used to construct an expression cassette that can be introduced into the desired host. Isolated nucleic acids of the present invention can be introduced according techniques known in the art. Generally, expression cassettes as described above and suitable for transformation of are prepared.

For single-celled organisms and organisms that can be regenerated from single cells, transformation can be carried out by in vitro culture, followed by selection for transformation and regeneration of transformants. Methods often used for transferring DNA or RNA into cells include microinjection, particle gun bombardment, forming DNA or RNA complexes with cationic lipids, liposomes or other carrier materials, electroporation, chemical methods, and viral methods. Other techniques are known in the art, for example see standard reference works such as Methods in Enzymology, Methods in Cell Biology, Molecular Biology Techniques, all published by Academic Press, Inc. NY. Methods for transforming various host cells are disclosed in Klein et al. "Transformation of microbes, plants and animals by particle bombardment", *Bio/Technol*. New York, N.Y., Nature Publishing Company, March 1992, 10(3):286-291. Waters has recently demonstrated the stable transfer of nucleic acids from bacteria to cultured mammalian cells, apparently via cell conjugation (Waters, V L 2001 *Nature Genetics* 29:375-376).

Transfer of the polynucleotide into the cell nucleus occurs by cellular processes and can sometimes be aided by choice of an appropriate vector, by including integration site sequences which can be acted upon by an intracellular transposase or recombinase. For reviews of transposase or recombinase mediated integration see, e.g., Craig, N L K (1988) *Ann Rev Genet*. 22:77; Cox, M M (1988) In *Genetic Recombination* (Kucherlapati and Smith, Eds.) pp. 429-443, American Society for Microbiology, Washington, D.C.; Hoess, R H et al. (1990) In *Nucleic Acid and Molecular Biology* (Eckstein and Lilley, Eds.) Vol 4, pp. 99-109, Springer-Verlag, Berlin.

Direct transformation of multicellular organisms can often be accomplished at an embryonic stage of the organism. For example, in *Drosophila*, as well as other insects, DNA can be microinjected into the embryo at a multinucleate stage where it can become integrated into many nuclei, some of which become the nuclei of germ line cells. Recently, stable germline transformations were reported in mosquito (Catteruccia, F., et al. (2000) Nature 405:954-962). By incorporating a marker as a component of the transforming DNA, non-chimeric progeny of the original transformant can be identified and maintained. Direct microinjection into egg or embryo cells has also been employed effectively for transforming many species, *Xenopus* for example. In the mouse, the existence of pluripotent embryonic stem (ES) cells that are amenable to culture in vitro has been used to generate transformed mice. The ES cells can be transformed in culture, then microinjected into mouse blastocysts, where they integrate into the developing embryo and generate germline chimeras. By interbreeding heterozygous siblings, homozygous animals carrying the desired gene can be obtained. For reviews of the methods for transforming multicellular organisms see, e.g., Haren et al. (1999) *Ann Rev Microbiol* 53:245-281; Reznikoff et al. (1999) *Biochem Biophys Res Comm* 266(3):729-734; Ivics et al. (1999) *Methods in Cell Biology* 60:99-131; Weinberg, E S (1998) *Curr Biol* 8(7):R244-247; Hall et al. (1997) *FEMS Microbiol Rev* 21(2):157-178; Craig (1997) *Ann Rev Biochem* 66:437-474; Beall et al. (1997) *Genes Dev* 11 (16): 2137-2151.

Techniques for transforming a wide variety of higher plant species are well known and described in the technical, scientific, and patent literature. See, for example, Weising et al., *Ann. Rev. Genet.* 22: 421-477 (1988). For example, the DNA construct may be introduced directly into the genomic DNA of the plant cell using techniques such as electroporation, PEG-mediated transfection, particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp. 197-213 in Plant Cell, Tissue and Organ Culture, Fundamental Methods. eds. O. L. Gamborg and G. C. Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski et al., *Embo J*. 3: 2717-2722 (1984). Electroporation techniques are described in Fromm et al., *Proc. Natl. Acad. Sci*. 82:5824 (1985). Ballistic transformation techniques are described in Klein et al., *Nature* 327:70-73 (1987).

*Agrobacterium tumefaciens*-meditated transformation techniques are well described in the scientific literature. See, for example Horsch et al., *Science* 233: 496-498 (1984), and Fraley et al., *Proc. Natl. Acad. Sci.* 80: 4803 (1983). For instance, *Agrobacterium* transformation of maize is described in U.S. Pat. No. 5,550,318.

Other methods of transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J. In: DNA Cloning, Vol. 11, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., Plant Cell Physiol. 25:1353, 1984), (3) the vortexing method (see, e.g., Kindle, *Proc. Natl. Acad. Sci., USA* 87:1228, (1990).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter,* 6:165 (1988). Expression of polypeptide coding nucleic acids can be obtained by injection of the DNA into reproductive organs of a plant as described by Pena et al., *Nature,* 325:274 (1987). DNA can also be injected directly into the cells of immature embryos and the rehydration of desiccated embryos as described by Neuhaus et al., *Theor. Appl. Genet.,* 75:30 (1987); and Benbrook et al., in Proceedings Bio Expo 1986, Butterworth, Stoneham, Mass., pp. 27-54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm et al., *The Plant Cell,* 2:603-618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* can be achieved as described by Horsch et al., *Science,* 227:1229-1231 (1985) and Fraley et al., *Proc. Natl. Acad. Sci. U.S.A.,* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally by Klee et al., *Ann. Rev. of Plant Phys.* 38: 467-486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, The Maize Handbook, Freeling and Walbot, Eds., Springer, New York (1994); Corn and Corn Improvement, 3rd edition, Sprague and Dudley Eds., American Society of Agronomy, Madison, Wis. (1988).

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated polynucleotide of interest. Progeny and variants, and mutants of the regenerated plants are also included within the scope of the invention, provided that these parts comprise the introduced nucleic acid sequences.

Transgenic plants expressing a selectable marker can be screened for transmission of the polynucleotide of interest, for example, standard DNA detection techniques to detect the polynucleotide, and/or immunoblots to detect protein expression. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

Plants that can be used in the method of the invention vary broadly and include monocotyledonous and dicotyledonous plants including corn, soybean, sunflower, sorghum, canola, wheat, alfalfa, cotton, rice, barley, potato, tomato, and millet.

Seeds derived from plants regenerated from transformed plant cells, plant parts or plant tissues, or progeny derived from the regenerated transformed plants, may be used directly as feed or food, or further processing may occur.

One of skill will recognize that after the expression cassette is stably incorporated in transgenic plants and confirmed to be operable, it can be introduced into other plants by sexual crossing. Any of a number of standard breeding techniques can be used, depending upon the species to be crossed. Further, one of skill will recognize that any component of the method can be introduced to the host organism by sexually crossing the target host with a donor organism which comprises one of more of the following: a targeting vector, and/or a replicase expression cassette, a site-specific recombinase expression cassette, or a transposase expression cassette. In the case of cells in culture, the components may also be brought together by fusing target cells and donor cells.

Any method described above in reference to plants can be applied to the generation and identification of gene targeting events in other target host organisms. Examples of organisms which can be used in the invention include, but are not limited to: insects, including *Coleoptera, Diptera*, such as *Drosophila, Hemiptera, Homoptera, Hymenoptera, Lepidoptera*, and *Orthoptera*; plants, including both monocotyledonous and dicotyledonous plants such as, but not limited to, maize, rice, wheat, oats, barley, sorghum, millet, soybean and other legumes, canola, *Brassica*, alfalfa, sunflower, safflower, *Arabidopsis*, cotton, potato, tomato, tobacco and the like; animals including mice, rats, sheep, pigs, bovines, amphibians, such as *Xenopus*, fish, such as zebrafish, birds; and protozoa such as ciliates, and/or parasitic protozoa, and the like.

Identification and Characterization of Modified Target Cells and Organisms

Gene targeting can be performed without selection, if there is a sensitive method for identifying recombinants, for example if the targeted gene modification can be easily detected by PCR analysis, or if it results in a certain phenotype. However, in most cases, identification of gene targeting events will be facilitated by the use of markers. Markers useful in the invention include positive and negative selectable markers as well as markers that facilitate screening, such as visual markers. Selectable markers include genes carrying resistance to an antibiotic such as spectinomycin (e.g. the aada gene), streptomycin (e.g., aada, or SPT), kanamycin (e.g., nptII), hygromycin (e.g., HPT), gentamycin, phleomycin, zeocin, or bleomycin, or resistance to a herbicide such as phosphinothricin (bar gene), or sulfonylurea (acetolactate synthase—ALS), genes that fulfill a growth requirement on an incomplete media such as HIS3, LEU2, URA3, LYS2, and TRP1 genes in yeast, and other such genes known in the art. Negative selectable markers include cytosine deaminase (codA) (Stougaard 1993 *Plant J.* 3:755-761), tms2 (DePicker et al. 1988 *Plant Cell Rep.* 7:63-66), nitrate reductase (Nussame et al. 1991 *Plant J.* 1:267-274), and SU1 (O'Keefe et al. 1994 *Plant Physiol.* 105:473-482). Screenable markers include fluorescent proteins such as green fluorescent protein (GFP) (Chalfie et al., 1994 *Science* 263:802; U.S. Pat. No. 6,146,826; U.S. Pat. No. 5,491,084; and WO 97/41228), reporter enzymes such as β-glucuronidase (GUS) (Jefferson R. A. 1987 *Plant Mol. Biol. Rep.* 5:387; U.S. Pat. No. 5,599,670; and U.S. Pat. No. 5,432,081), β-galactosidase (lacZ), alkaline phosphatase (AP), glutathione S-transferase (GST) and luciferase (U.S. Pat. No. 5,674,713; and Ow et al. 1986 *Science* 234(4778):856-859), visual markers such as color markers like anthocyanins such as CRC (Ludwig et al. 1990 *Science* 247(4841):449-450) R gene family (e.g. Lc, P, S), A, C, R-nj, body and/or eye color genes in *Drosophila*, and coat color genes in mammalian systems, and others known in the art.

One or more markers may be used in order to select and screen for gene targeting events. One common strategy for gene disruption involves using a target modifying polynucleotide in which the target is disrupted by a promoterless selectable marker. Since the selectable marker lacks a promoter, random integration events are unlikely to lead to transcription of the gene. Gene targeting events will put the selectable marker under control of the promoter for the target gene. Gene targeting events are identified by selection for expression of the selectable marker. Another common strategy utilizes a positive-negative selection scheme. This scheme utilizes two selectable markers, one that confers resistance ($R^+$) coupled with one that confers a sensitivity ($S^+$), each with a promoter. When this polynucleotide is randomly inserted, the resulting phenotype is $R^+/S^+$. When a gene targeting event is generated, the two markers are uncoupled and the resulting phenotype is $R^+/S^-$. Examples of using positive-negative selection are found in Thykjaer et al. (1997) *Plant Mol. Biol.* 35:523-530; and WO 01/66717, which are herein incorporated by reference.

Cells or organisms identified by one or more selective markers can be further screened for modification of the target polynucleotide of interest by a large number of molecular and biochemical assays known in the art. For example, standard DNA detection techniques to detect the polynucleotide including amplification techniques such as restriction enzyme analysis, PCR, Southern and Northern blots, DNA chips, in situ hybridization, sequencing and the like. PCR is fast, specific and sensitive method commonly used to detect gene targeting events. Primers that distinguish between unmodified and modified target are designed and amplification conditions identified as known to those of skill in the art, see for example standard references such as Sambrook et al. (1989) *Molecular Cloning, A Laboratory Manual* $2^{nd}$ Ed. Cold Spring Harbor Press New York, Walker and Gaastra, eds. (1983) *Techniques in Molecular Biology*, MacMillan Publishing New York, Innis et al. eds. (1990) *PCR Protocols: A Guide to Methods and Applications*, Academic Press, Inc. San Diego, Calif., Ausubel et al., eds. (1995) *Current Protocols in Molecular Biology*, Greene Publishing and Wiley-Interscience, New York. See also, Kim and Smithies (1988) *Nucl. Acids Res.* 16:8887-8903. Biochemical and/or immunochemical assay to detect and/or quantify protein expression may also be employed, such as immunoblots, immunoprecipitation, ELISA assays, immunohistochemistry, enzyme activity assays, enzyme kinetic studies, chromatographic and electrophoretic separations such as polyacrylamide gel profiles, capillary electrophoresis, protein binding/interaction assays such as ligand binding, gel shift assays, blot overlays, co-immunoprecipitation, and the like. Standard techniques for RNA analysis can be employed and include PCR amplification assays using oligonucleotide primers designed to amplify only the modified RNA templates and solution hybridization assays using heterologous nucleic acid-specific probes. In addition, in situ hybridization and immunocytochemistry according to standard protocols can be done using heterologous nucleic acid specific polynucleotide probes and antibodies, respectively, to localize sites of expression within transgenic tissue.

The present invention will be further described by reference to the following detailed examples.

It is understood, however, that there are many extensions, variations, and modifications on the basic theme of the present invention beyond that shown in the examples and description, which are within the spirit and scope of the present invention. All publications, patents, and patent applications cited herein are hereby incorporated by reference.

EXAMPLES

Example 1

Replicating Vectors and Recombination

Vector construction was done using standard molecular biology techniques. T-DNA vectors were constructed to test whether recombinant T-DNA molecules could be produced and could persist in transformed maize cells using a viral replication mechanism acting in concert with recombination.

The recombination event could be site-specific, homologous or illegitimate recombination. The basic vector design comprised at least one source of microhomology that could be used to circularize the T-DNA. For example, overlapping areas of the neo gene, FRT1 sites, or the left and right T-DNA borders can be used as the regions of microhomology. A recombination event within the neo gene, FRT1 sites, or the border sequences should generate replication competent, circular T-DNAs which therefore leads to the activation of a recombination marker gene, for example neo which confers kanamycin-resistance, or gusA. In order to recover replicating T-DNA molecules from *E. coli*, the ampicillin-resistance gene was incorporated into the T-DNA structure. A FLP recombinase gene, driven by a separate promoter, can be provided on the same T-DNA or provided by another vector.

A. The Effect of Replicase Expression on Homologous Recombination of T-DNA

TABLE I

| Plasmid | Description | Neo | Rep |
|---|---|---|---|
| P10525 | RB-Ubipro/intron-GUS-Ubi-Bar-LB | No | No |
| P16821 | LB-3'Δneo-Rep-WDVLIR-Ubipro/intron-GUS-AMP-5'Δneo-RB | Inactive | Yes |
| P16822 | RB-3'Δneo-Rep-WDVLIR-Ubipro/intron-GUS-AMP-5'Δneo-LB | Inactive | Yes |
| P16823 | RB-3'Δneo-WDVLIR-Ubipro/intron-GUS-AMP-5'Δneo-LB | Inactive | No |
| P16824 | RB-neo-Rep-WDVLIR-Ubipro/intron-GUS-AMP-LB | Active | Yes |

Two truncated inactive neo genes on the same T-DNA were used to monitor the homologous recombination between T-DNAs in BMS cells. One neo gene has a 5' deletion (5'Δneo), while the second gene has a 3' deletion (3'Δneo), both truncated fragments share a significant region of overlapping homology comprising 653 bp. Experiments were done in either the presence or absence of WDV Replicase (Rep). If homologous recombination occurs, inactive neo genes are restored to produce an active, full-length neo gene and the cells acquire kanamycin-resistance.

BMS cells were transformed with the vectors of Table 1 according to the *Agrobacterium*-mediated transformation protocol illustrated in Example 3A. Plasmid P10525 is a positive control transformation vector. Untransformed BMS cells were used as the negative control.

T-DNA recombinants were identified by the ability to transform *E. coli*. In order to test for recombinants, DNA was isolated from untransformed BMS cells (negative control) and transformed BMS cells. Further, to determine if the T-DNAs could recombine in *Agrobacterium*, DNA was isolated from the strains used for *Agrobacterium*-mediated transformation of BMS cells.

DNA was isolated from 2 ml aliquots of *Agrobacterium* 3 hours after acetosyringone induction. Plasmid DNA was isolated using the Qiagen DNA mini-prep kit (Qiagen, Valencia, Calif.) according to the manufacturer's instructions. An aliquot of each sample was adjusted to a standard concentration of 17 ng/μl and used for further analysis. All DNA samples were stored at −20° C.

DNA was extracted from BMS cells harvested 7 days after co-cultivation with *Agrobacterium* using the DNeasy Plant Mini Kit (Qiagen, Valencia, Calif.) according to the manufacturer's instructions. Briefly, 100 mg of BMS cells were ground to a fine powder in pre-chilled mortars and liquid nitrogen. 400 μl of extraction buffer (buffer AP1) and 4 μl of Rnase A stock (100 mg/ml) were added to the ground cells. Isolated DNA was eluted in either water or buffer AE. DNA concentration was estimated using the PicoGreen dsDNA quantitation kit (Molecular Probes, Eugene, Oreg.). An aliquot of each DNA sample was adjusted to 17 ng/μl. All DNA samples were stored at −20° C.

Forty microliters of library-efficiency DH5α *E. coli* (GibcoBRL) was transformed with 24 ng of DNA from each treatment by electroporation. The electroporation was performed in a Bio-Rad Gene Pulser (Bio-Rad, Hercules, Calif.) at 2.5 KV with capacitance set at 25 μF, resistance set at 200 ohms and time set at constant using 2 mm cuvettes. Electroporated cells were incubated in 0.6 ml of 2×YT media at 37° C. for 30 min. After incubation, 0.2 ml samples were dispensed onto agar plates containing LB medium supplemented with 0.1 g/L ampicillin. The plates were incubated overnight at 37° C., the number of colonies per plate was counted. The number of recovered colonies per plate was averaged for each treatment.

Forty colonies were randomly picked and inoculated onto LB agar plates containing kanamycin (0.1 g/L) to screen for homologous recombinants. The results of this screen are shown in Table 2.

TABLE 2

Kanamycin resistance generated by homologous recombination of T-DNA

| | | Ampicillin-resistant colonies | |
|---|---|---|---|
| Transformation | Total | Kan-Resistant | % |
| BMS only | 0 | 0 | 0 |
| Agro only | 77 | 1/20 | 5 |
| BMS + Agro | 39 | 0/20 | 0 |
| BMS + (Agro + Rep) | 313 | 65/80 | 82 |

Number of recovered, ampicillin- and kanamycin-resistant colonies after *E. coli* electroporation with DNA isolated from BMS cells only, *Agrobacterium* only, or BMS cells co-cultivated with *Agrobacterium*.
BMS + Agro: DNA from BMS cells co-cultivated with *Agrobacterium* containing T-DNA without the rep gene (P16823)
BMS + (Agro + rep): DNA from BMS cells co-cultivated with *Agrobacterium* containing T-DNA (P16821 or P16822) with the rep gene
The column labeled as "Total" presents the total number of ampicillin-resistant colonies recovered from each particular treatment.
The column "Kan-Resistant" presents the fraction of kanamycin-resistant colonies recovered among the tested ampicillin-resistant colonies.

These results indicate that homologous recombination did not occur in the *Agrobacterium* harboring the T-DNA, it only occurred in the transformed BMS cells. Further, these results indicate that homologous recombination occurred only in the presence of replicase (Rep), when Rep was deleted, no kanamycin-resistant colonies were recovered. Once the rep gene was provided, 82% of the ampicillin-resistant colonies were also kanamycin-resistant.

In order to show that the homologous recombination occurred in the BMS cells and was not an artifact from the later *E. coli* transformation, isolated putative recombinant T-DNAs were subjected to exonuclease III treatment and used to transform *E. coli* as described above. The exonuclease degrades linear DNA while circular recombinants are not affected. No difference in transformation efficiency was observed between untreated and exonuclease III-treated T-DNAs. These results indicate that homologous recombination occurred in the BMS cells and was not an artifact of *E. coli* transformation.

A restriction digest followed by electrophoretic separation was used to confirm that the kanamycin-resistant lines contained a restored full-length neo gene. A SacII restriction site was located upstream of the neo gene and a SphI site was located downstream of the neo gene. If the neo gene is restored via homologous recombination to a full-length gene, a SacII/SphI restriction digest yields a band of 1009 bp on an agarose gel. If the truncated neo gene has not been restored to full-length by recombination, a SacII/SphI restriction digest yields a band of 847 bp on an agarose gel. Control plasmids and DNA from 13 kanamycin-resistant and 2 kanamycin-sensitive lines were subjected to SacII/SphI restriction enzyme digestion and agarose gel separation. Results confirm that 11 of the 13 kanamycin-resistant lines had a band at 1009 bp consistent with the restoration of a full-length neo gene by homologous recombination in BMS cells, the other two kanamycin resistant lines showed two bands of slightly >1009 bp and ≦847 bp, likely indicating an additional rearrangement of the recombined neo gene. Both kanamycin-sensitive lines lacked the presence of the 1009 bp band indicative of a full-length neo gene.

PCR analysis was also used to confirm that kanamycin-resistance was due to the restoration of a full-length neo gene by homologous recombination.

B. Functional Replicase is Required to Increase Homologous Recombination

The pWI-11 vector was the source of the wheat dwarf virus (WDV) initiator protein gene (rep) (Ugaki, M. et al. (1991) *Nucl. Acids Res.* 19:371-377). An NcoI-SacI fragment of this vector containing the rep coding sequence and the short intergenic region (SIR) was subcloned into the multiple cloning site of pUC19. The long intergenic region (LIR) regulatory element was amplified by PCR to produce a BamHI-NcoI fragment, which was subsequently ligated with the rep NcoI-SphI fragment and cloned into the BamHI/SphI restriction sites of a gusA expression vector. This three-fragment ligation produced an expression vector containing gusA and rep, whose expression was controlled by the bi-directional (divergent) promoters within the LIR region. The LIR region also contained the origin of replication (ori) required for vector amplification in plant cells. Subsequently, the gusA gene was modified to include the potato ST LS1 intron (Vancanneyt, G. et al., (1990) *Mol. Gen. Genet.* 220:245-250). The maize ubi1 intron (Christensen and Quail (1996) *Transgenic Res.* 5:213-218) containing an FRT1 site was inserted between the LIR promoter and the gusA coding sequence.

In order to produce T-DNA vectors, a synthetic FRT1 site (48 bp) was inserted into the multiple cloning site between two T-DNA border sequences in pSB11 (Ishida, Y. et al. (1996) *Nat. Biotech.* 14:745-750). The gusA/rep-containing vectors, which included the plasmid backbone with the ampicillin-resistant gene, were integrated into this site by in-vitro site-specific recombination catalyzed by the FLP protein. The reaction contained 25 mM Tris-HCl, pH 7.4, 1 mM EDTA, 1 mM DTT, 5% glycerol, 0.1 mM NaCl, 2 µg each of the FRT1-containing vectors to be integrated, and 1.4 µg of FLP protein in a total volume of 10 µl. Incubation was for 60 min at 30° C. Two microliters of the incubation mixture were used for transformation of library efficiency DH5α*E. coli* competent cells (Cat#18263-012, Invitrogen, Carlsbad, Calif.) according to the manufacturer's specifications. Bacterial colonies were grown at 37° C. overnight in spectinomycin-containing (100 mg/L) LB medium and then transferred into 2 ml of ampicillin-containing (100 mg/L) liquid LB medium for identification and DNA preparation of double-antibiotic-resistant, co-integrative plasmids.

Five vectors were generated as shown in Table 3 below. In experimental constructs, the gusA gene is separated from its promoter by T-DNA border sequences. Any recombination event within the FRT1 sites or the border sequences will generate replication competent circular T-DNAs in which the recombination marker gene, gusA, is activated. SUG indicates an opposite orientation of the gusA gene in relation to its promoter on the other end of the T-DNA. Two promoters were used to drive the expression of gusA, a maize ubiquitin promoter (Upro) was used in the transformation control vectors (Upro-SUG and Upro-GUS), and v-sense promoter (Wpro) of WDV was used in the experimental vectors (Wpro-SUG, W-proRep-SUG, and WproRepm-SUG). The v-sense promoter is part of the LIR compact viral genetic element. This element also contains the viral (+)strand DNA replication origin (ori) and regulatory sequences controlling expression of the WDV initiator protein (Rep).

Tri-parental mating or electroporation was used to integrate the pSB11-based vectors into the super-binary vector pSB1 residing in *Agrobacterium tumefaciens* strain LBA 4404. Co-integrates were identified by double selection of transformed *Agrobacterium* colonies on media containing spectinomycin and tetracyclin at 100 mg/L each. Restriction analysis was used to verify the structural integrity of the super-binary vectors.

TABLE 3

GUS constructs

| Plasmid | Description | Rep |
|---|---|---|
| WproRepm-SUG | RB-FRT1/Ubi3'intron-3'gusA-Amp$^r$-LIR/Repm-Ubi5'intron-FRT1-LB | No |
| WproRep-SUG | RB-FRT1/Ubi3'intron-3'gusA-Amp$^r$-LIR/Rep-Ubi5'intron-FRT1-LB | Yes |
| Wpro-SUG | RB-FRT1/Ubi3'intron-3'gusA-Amp$^r$-LIR-Ubi5'intron-FRT1-LB | No |
| Upro-SUG | RB-FRT1-Ubi3'intron-3'gusA-Amp$^r$-Ubipro-Ubi5'intron-FRT1-LB | No |

TABLE 4

Recovery of T-DNAs

| | Number of colonies/plate | |
|---|---|---|
| Plasmid | 3 Days | 6 Days |
| WproRepm-SUG | 28 ± 4 | 10 ± 8 |
| WproRep-SUG | 25 ± 6 | 170 ± 20 |
| Wpro-SUG | 13 ± 1 | 18 ± 4 |
| Upro-GUS | 1 ± 0 | 0.5 ± 0.7 |

BMS cells were transformed with the vectors of Table 3 as described in Example 3A. Circular, recombinant T-DNAs were recovered from total DNA preparations obtained from BMS cells three and six days after transformation (see Table 4) and used to transformation of DH5α *E. Coli* as described earlier. In the WproRep-SUG treatment, more ampicillin-resistant colonies were observed using DNA isolated from BMS cells six days after transformation compared to DNA isolated three days after transformation. No such increase was seen in the Wpro-SUG treatment, where the vector lacks the initiator protein (rep) gene, or in the WproRepm-SUG treatment, where the C2 open reading frame of the initiator rep gene was mutated to eliminate replication function. These results indicate that more recombinant T-DNA molecules are produced in BMS cells in the presence of the WDV replicase six days after transformation. Since the initiation of T-DNA recombination/replication requires accumulation of the rep gene product, the process is apparently delayed compared to a direct expression of transformation marker genes in transgenic BMS cells (see also Table 6).

TABLE 5

Recovery of T-DNAs +/− FLP

| | Number of colonies/plate | | | |
|---|---|---|---|---|
| | 3 Days | | 6 Days | |
| Plasmid | −FLP | +FLP | −FLP | +FLP |
| WproRep-SUG | 25 ± 6 | 28 ± 6 | 170 ± 20 | 504 ± 107 |
| Wpro-SUG | 13 ± 1 | 20 ± 3 | 18 ± 4 | 20 ± 9 |

The circular, recombinant T-DNAs can be formed by site-specific recombination at the FRT1 sites, or by homologous recombination at the T-DNA borders. As analyzed by PCR, in the absence of FLP, junction sites are generated mostly by the recombination around the border sequences, as indicated by a 661 bp PCR product resulting from border-to-border recombination. In the presence of FLP, the size of the predominant PCR product is smaller and corresponds to the expected size of the FRT-recombined T-DNA molecules of 307 bp. Generation of these molecules was independent of the method of FLP delivery, as the FLP expression unit was provided on the same T-DNA, delivered by co-transformation, or by a combination of both methods. Further, in treatments with FLP, no PCR amplification signal was observed from the border-to-border junction.

Circular T-DNA molecules recovered 6 days after co-cultivation were analyzed further. No recombinant T-DNA molecules were recovered from treatments containing only FLP with no Rep. A random sample of 27 recombinant T-DNAs was sequenced through the recombination sites to verify that they were generated by site-specific recombination. Of those 27 T-DNAs sequenced, 20 T-DNA junction sites were the result of recombination events within the two FRT1 sites, presumably catalyzed by FLP.

TABLE 6

GUS expression

| | GUS expression (nmol MU/min/PCV BMS cells) Days after Transformation | | | | | | |
|---|---|---|---|---|---|---|---|
| Plasmid | 1 | 2 | 3 | 4 | 5 | 6 | 7 |
| No DNA | 4 | 6 | 7 | 7 | 7 | 6 | 6 |
| WproRep-SUG | 13 | 16 | 11 | 52 | 134 | 395 | 518 |
| Upro-SUG | 6 | 10 | 38 | 37 | 58 | 92 | 52 |
| Upro-GUS | 8 | 78 | 179 | 242 | 275 | 278 | 277 |

The gusA gene separated from its promoter by T-DNA border sequences produced strong GUS activity in BMS cells co-cultivated with an *Agrobacterium* strain containing the WproRep-SUG T-DNA (see Table 6). Expression of GUS was delayed by about 1-2 days as compared to the fully functional gusA expression cassette, Upro-GUS, which was used as a positive control. This delay could not be attributed to background activity since the Upro-SUG control showed only a fraction of the GUS activity observed in the WproRep-SUG treatment. In addition, no GUS activity was detectable when the ubiquitin promoter in Upro-GUS was replaced with the LIR promoter. The LIR promoter is only activated in the presence of the initiator Rep protein. These results indicate a functional gusA gene was generated by a concomitant recombination and replication of T-DNAs.

A sample of recombinant T-DNA molecules recovered from treatments with the Wpro-SUG vector was sequenced to determine the junction sites around the left border. Among 44 randomly selected clones, 33 produced sequencing data. Among them, only two recombinant T-DNAs originated from recombination events at the same site, i.e. 2 of 33 events had the same junction sequence. One recombination junction site was identified within the FRT sequences sharing a perfect 76 bp homology, but FLP protein was not provided in this particular treatment, therefore the recombination was based on sequence homology and not produced by the action of a site-specific recombinase. These results indicate the population of recombinant T-DNAs generated is likely highly heterogeneous and may not originate from a limited number of T-DNA recombination events.

Sequence analysis of the LB junction sites indicated a variety of structural features. While no precise right and left border T-DNA junctions were identified, two intact RB ends and one LB ends were found in conjunction with the other modified T-DNA ends. Microhomologies ranging from 1 to 6 bp were common at the crossover sites. Four examples of filler DNA at the junction sites were found. The sequencing primer was positioned about 350 bp from the left border, which biased the analysis towards recovery of left border junction sequences. Nonetheless, 75% of randomly selected clones produced sequencing data indicating that left border recombination was a preferred mode for generating recombinant T-DNAs.

Example 2

Vectors for Plant Transformation

Vector construction is done using standard molecular biology techniques. The method of transformation is not critical to the invention, therefore any method of transformation can be used, and vector construction and/or insert preparation can be modified accordingly.

A. Introduced Transgene and Targeting Vector i. Introduced GUS Transgene

An *Agrobacterium* transformation vector was constructed containing a GUS expression cassette between the left and right borders. The GUS expression cassette comprised 5'UTR::Ubiquitin promoter::maize ubiquitin intron 1::gusA exon 1::gusA intron 1::gusA exon 2::pinII terminator:: 3'UTR. The 5' and 3' regions each have one SphI site. SphI restriction enzyme digestion produces a 6.0-6.5 kb DNA fragment. PCR primers hybridizing to ubi intron 1 and gusA intron 2 amplify a 0.7 kb fragment. The overall structure of the transgene is as follows:

5' ubi pro::ubi intron 1::gusA exon 1::gusA intron 1::gusA exon 2::pinII 3' ii. GUS Targeting Vector

The introduced gusA transgene was used as a target site for a gene targeting experiment. The gene targeting vector was contained between the left and right border in an *Agrobacterium* transformation vector. The gene targeting vector was designed to replace gusA exon 1 with a bar selectable marker gene which contains a SphI site. Restriction digestion with SphI now results in a 2.3 kb fragment. PCR amplification with the primers directed to introns 1 and 2 generates a 1.1 kb fragment. Removal of the gusA exon 1 eliminates GUS expression.

The structure of the gene targeting vector is as follows:

5'LB-ubi pro::ubi intron 1::bar::gusA intron 2::gusA exon 2-LIR::Rep::SIR-RB 3' wherein LIR is the Wheat Dwarf Virus (WDV) long intergenic region containing the promoter and origin of replication; Rep is the WDV replicase gene; and SIR is the WDV short intergenic region containing polyadenylation signals.

B. Gene Targeting System for an Endogenous Genomic Target Site: Acetohydroxy-Acid Synthase (AHAS)

Point mutations in acetohydroxy-acid synthase (AHAS) can be introduced to confer either a sulfonylurea or imidazolinone herbicide resistance phenotype in plants.

i. Tobacco

There are two genetically unlinked AHAS loci, SuRA and SuRB, in *Nicotiana tabacum*, herbicide resistance can be mediated by mutation at either locus (Chaleff et al. (1986) in Molecular Strategies for Crop Protection: UCLA Symposium on Molecular and Cellular Biology, 48:415-425, Arntzen and Ryan Eds, John Wiley and Sons, NY; Lee et al. (1988) *EMBO J.* 7:1241-1248). For example, a sulfonylurea herbicide resistance phenotype can be generated in tobacco by targeted modification of SuRB to convert Trp 573-Leu 573 (W573L) as described by Lee et al. (1990) *Plant Cell* 2:415-425. The targeting vectors used in Lee et al. (supra) can be modified to enhance gene targeting frequency by the inclusion of an origin of replication (ori) and a replicase expression cassette. Using standard vector construction and molecular biology techniques, gene targeting vector pAGS182BV is modified as follows:

3'RB-5'ΔAHAS-3'ocs::nptII::pnos-3'ocs::Rep::pnos-ori-LB 5' wherein 5'ΔAHAS indicates a 5' deleted version of the SurB gene containing the W573L mutation as described by Lee et al. (supra). The resulting vector will be referenced as pAGS182Bvrep. Vector pAGS180BV can be modified in a similar way.

ii. Maize

Two AHAS genes, AHAS108 and AHAS109, have been reported in maize (Fang et al. (1992) *Plant Mol. Biol.* 18:1185-1187), herbicide resistance can be generated by mutation at either locus. For example, a sulfonylurea herbicide resistance phenotype can be generated in maize by a targeted modification of AHAS108 to convert Pro 165-Ala 165 (P165A) as described by Lee et al. (1988) *EMBO J.* 7:1241-1248. An imidazolinone herbicide resistance phenotype can be generated in maize by a targeted modification of AHAS108 to convert Ser 621-Asn 621 (S621N) as described by Sathasivan et al. (1991) *Plant Physiol.* 97:1044-1050.

Using standard vector construction and molecular biology techniques, targeting vectors can be constructed as follows:

5' LB-ori-ubi::Rep::nos-AHAS108 S621N-RB 3'
5' LB-ori-ubi::Rep::nos-AHAS108 P165A-RB 3'

The mutant AHAS genes are not operably linked to a promoter, therefore random integration is unlikely to yield a herbicide resistant phenotype.

C. Targeting Vectors Introduced by Sexual Crosses

In order to be maintained for delivery via sexual crosses, the targeting vector must be integrated into the genome of a plant and excised after crossing to a second plant. Therefore the targeting vector must be flanked by excision sequences, for example site-specific recombination sites or transposon terminal repeats. This example outlines a strategy using a site-specific recombinase.

The targeting vector is flanked at the 5' and 3' ends by directly repeated FRT sequences. Adjacent to the 5' FRT (i.e. directly inside the FRT site) is the Wheat Dwarf Virus replicase gene (the Rep C1:C2 sequence). Adjacent to the 3' FRT site (i.e. directly inside the site) is a promoter, for example the Wheat Dwarf Virus LIR which contains the viral promoter elements and the viral origin of replication (ori). In the center of the cassette (i.e. in between the LIR and the replicase gene) is the mutant AHAS sequence (i.e. the target-modifying sequence). This arrangement is shown below:

5' FRT-replicase-mutant AHAS-LIR (Promoter & ori)-FRT 3'

Outside the targeting vector, but within the T-borders, is a selection cassette, for example UBI::bar::pinII. The transformation cassette is shown below:

5' LB-ubi::bar::pinII-FRT-replicase-mutant AHAS-LIR-FRT3'

Example 3

Transformation

This example provides methods of plant transformation and regeneration using the polynucleotides of the present invention. The method of transformation is not critical to the invention, therefore any method of transformation can be used.

A. *Agrobacterium*-Mediated Transformation of BMS Cells

*Zea mays* Black Mexican Sweet (BMS) cells were propagated in Murashige and Skoog medium containing 4.3 g/L MS salts, 3% sucrose, 2 mg/L 2,4-D, 0.1 g/L myoinositol, 0.5 mg/L nicotinic acid, 0.1 mg/L thiamine-HCL, 0.5 mg/L pyridoxine-HCL, and 2 mg/L glycine, pH 5.6. The suspension cultures were shaken at 125 rpm at 25° C. in the dark. For transformation, aliquots of cell suspension (5 ml, 0.4 packed cell volume/ml) were transferred into 50-ml conical tubes and the MS medium was replaced with 5 ml of N6 medium (4 g/L N6 basal salts, 6.85% sucrose, 1.5 mg/L 2,4-D, 0.69 g/L L-proline, 0.5 mg/L thiamine-HCl, and 1× Eriksson's vitamin mix, pH 5.2) supplemented with acetosyringone at 0.1 mM concentration. The same medium (5 ml) was used to re-suspend the pellet of $2.5 \times 10^8$ *Agrobacterium* cells (centrifuged at 4K rpm for 15 min) that were grown overnight in 30 ml of a minimal medium containing 10.5 g/L $K_2HPO_4$, 4.5 g/L $KH_2PO_4$, 1 g/L ammonium sulfate, 0.5 g/L sodium citrate dihydrate, 1 mM magnesium sulfate, and 0.2% sucrose. The two cell suspensions, BMS cells and *Agrobacterium*, were combined and placed on a gyratory shaker at 140 rpm for 3 hrs at 27° C. in the dark. Fifty μl samples of the BMS/*Agrobacterium* co-cultivation mixtures were placed on dry glass microfiber filters (VWR Scientific Products), and transferred onto the N6 co-cultivation medium similar to the one used for the initial pre-incubations but containing 3% sucrose, 2 mg/L 2,4-D, pH 5.8, and supplemented with 0.3% agar. Plates were incubated in the dark at 27° C. for 24 hrs. Filters were transferred onto the same media supplemented with 100 mg/L carbenicillin to eliminate *Agrobacterium*.

B. Particle Bombardment Transformation and Regeneration of Maize Callus

Immature maize embryos from greenhouse or field grown High type II donor plants are bombarded with a plasmid or insert containing polynucleotide of the invention. If the polynucleotide does not include a selectable marker, another plasmid containing a selectable marker gene can be co-precipitated on the particles used for bombardment. For example, a plasmid containing the PAT gene (Wohlleben et al. (1988) *Gene* 70:25-37) which confers resistance to the herbicide Bialaphos can be used. Transformation is performed as follows.

The ears are surface sterilized in 50% Chlorox bleach plus 0.5% Micro detergent for 20 minutes, and rinsed two times with sterile water. The immature embryos are excised and placed embryo axis side down (scutellum side up), 25 embryos per plate. These are cultured on 560L agar medium 4 days prior to bombardment in the dark. Medium 560L is an N6-based medium containing Eriksson's vitamins, thiamine, sucrose, 2,4-D, and silver nitrate. The day of bombardment, the embryos are transferred to 560Y medium for 4 hours and are arranged within the 2.5-cm target zone. Medium 560Y is a high osmoticum medium (560L with high sucrose concentration).

The plasmid or insert DNA for transformation is precipitated onto 1.1 μm (average diameter) tungsten pellets using a $CaCl_2$ precipitation procedure as follows: 100 μl prepared tungsten particles (0.6 mg) in water, 20 μl (2 μg) DNA in TrisEDTA buffer (1 μg total), 100 μl 2.5 M $CaCl_2$, 40 μl 0.1 M spermidine.

Each reagent is added sequentially to the tungsten particle suspension. The final mixture is sonicated briefly. After the precipitation period, the tubes are centrifuged briefly, liquid removed, washed with 500 ml 100% ethanol, and centrifuged again for 30 seconds. Again the liquid is removed, and 60 μl 100% ethanol is added to the final tungsten particle pellet. For particle gun bombardment, the tungsten/DNA particles are briefly sonicated and 5 μl spotted onto the center of each macrocarrier and allowed to dry about 2 minutes before bombardment.

The sample plates are bombarded at a distance of 8 cm from the stopping screen to the tissue, using a DuPont biolistics helium particle gun. All samples receive a single shot at 650 PSI, with a total of ten aliquots taken from each tube of prepared particles/DNA.

Four to 12 hours post bombardment, the embryos are moved to 560P (a low osmoticum callus initiation medium similar to 560L but with lower silver nitrate), for 3-7 days, then transferred to 560R selection medium, an N6 based medium similar to 560P containing 3 mg/liter Bialaphos, and subcultured every 2 weeks. After approximately 10 weeks of selection, callus clones are sampled for PCR and activity of the polynucleotide of interest. Positive lines are transferred to 288J medium, an MS-based medium with lower sucrose and hormone levels, to initiate plant regeneration. Following somatic embryo maturation (2-4 weeks), well-developed somatic embryos are transferred to medium for germination and transferred to the lighted culture room. Approximately 7-10 days later, developing plantlets are transferred to medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to Classic™ 600 pots (1.6 gallon) and grown to maturity. Plants are monitored for expression of the polynucleotide of interest.

C. *Agrobacterium*-Mediated Transformation and Regeneration of Maize Callus

For *Agrobacterium*-mediated transformation of maize, a gene targeting vector of the present invention is introduced using the method of Zhao (U.S. Pat. No. 5,981,840, and PCT patent publication WO98/32326; the contents of which are hereby incorporated by reference).

Briefly, immature embryos are isolated from maize and the embryos contacted with a suspension of *Agrobacterium* containing a polynucleotide of the present invention, where the bacteria are capable of transferring the nucleotide sequence of interest to at least one cell of at least one of the immature embryos (step 1: the infection step). In this step the immature embryos are immersed in an *Agrobacterium* suspension for the initiation of inoculation. The embryos are co-cultured with the *Agrobacterium* (step 2: the co-cultivation step). The immature embryos are cultured on solid medium following the infection step. Following this co-cultivation period an optional "resting" step is available. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

D. Transformation of Dicots

A polynucleotide of the present invention can be introduced into embryogenic suspension cultures of soybean by particle bombardment using the methods as essentially described in Parrott, W. A., L. M. Hoffman, D. F. Hildebrand, E. G. Williams, and G. B. Collins (1989) *Plant Cell Rep.* 7:615-617. This method, with modifications, is described below.

Seed is removed from pods when the cotyledons are between 3 and 5 mm in length. The seeds are sterilized in a bleach solution (0.5%) for 15 minutes after which time the seeds are rinsed with sterile distilled water. The immature cotyledons are excised by first cutting away the portion of the seed that contains the embryo axis. The cotyledons are then removed from the seed coat by gently pushing the distal end of the seed with the blunt end of the scalpel blade. The cotyledons are then placed (flat side up) SB1 initiation medium (MS salts, B5 vitamins, 20 mg/L 2,4-D, 31.5 g/l sucrose, 8 g/L TC Agar, pH 5.8). The petri plates are incubated in the light (16 hr day; 75-80 μE) at 26° C. After 4 weeks of incubation the cotyledons are transferred to fresh SB1 medium. After an additional two weeks, globular stage somatic embryos that exhibit proliferative areas are excised and transferred to FN Lite liquid medium (Samoylov, V. M., D. M. Tucker, and W. A. Parrott (1998) *In Vitro Cell Dev. Biol.-Plant* 34:8-13). About 10 to 12 small clusters of somatic embryos are placed in 250 ml flasks containing 35 ml of SB172 medium. The soybean embryogenic suspension cultures are maintained in 35 mL liquid media on a rotary shaker, 150 rpm, at 26° C. with florescent lights (20 μE) on a 16:8 hour day/night schedule. Cultures are sub-cultured every two weeks by inoculating approximately 35 mg of tissue into 35 mL of liquid medium.

Soybean embryogenic suspension cultures are then transformed using particle gun bombardment (Klein et al. (1987) *Nature* (London) 327:70; U.S. Pat. No. 4,945,050). A BioRad Biolistic™ PDS1000/HE instrument can be used for these transformations. A selectable marker gene, which is used to facilitate soybean transformation, is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is agitated for three minutes, spun in a microfuge for 10 seconds and the supernatant removed. The DNA-coated particles are washed once in 400 µL 70% ethanol and resuspended in 40 µL of anhydrous ethanol. The DNA/particle suspension is sonicated three times for one second each. Five µL of the DNA-coated gold particles is then loaded on each macro carrier disk.

Approximately 300-400 mg of a two-week-old suspension culture is placed in an empty 60×15 mm petri dish and the residual liquid removed from the tissue with a pipette. Membrane rupture pressure is set at 1100 psi and the chamber is evacuated to a vacuum of 28 inches mercury. The tissue is placed approximately 8 cm away from the retaining screen, and is bombarded three times. Following bombardment, the tissue is divided in half and placed back into 35 ml of FN Lite medium.

Five to seven days after bombardment, the liquid medium is exchanged with fresh medium. Eleven days post bombardment the medium is exchanged with fresh medium containing 50 mg/mL hygromycin. This selective medium is refreshed weekly. Seven to eight weeks post bombardment, green, transformed tissue will be observed growing from untransformed, necrotic embryogenic clusters. Isolated green tissue is removed and inoculated into individual flasks to generate new, clonally propagated, transformed embryogenic suspension cultures. Each new line is treated as an independent transformation event. These suspensions are then subcultured and maintained as clusters of immature embryos, or tissue is regenerated into whole plants by maturation and germination of individual embryos.

E. DNA Isolation i. DNA Isolation from Callus and Leaf Tissues

In order to screen putative transformation events for the presence of the transgene, genomic DNA is extracted from calluses or leaves using a modification of the CTAB (cetyl-triethylammonium bromide, Sigma H5882) method described by Stacey and Isaac (1994). Approximately 100-200 mg of frozen tissues is ground into powder in liquid nitrogen and homogenized in 1 ml of CTAB extraction buffer (2% CTAB, 0.02 M EDTA, 0.1 M Tris-HCl pH 8, 1.4 M NaCl, 25 mM DTT) for 30 min at 65° C. Homogenized samples are allowed to cool at room temperature for 15 min before a single protein extraction with approximately 1 ml 24:1 v/v chloroform:octanol is done. Samples are centrifuged for 7 min at 13,000 rpm and the upper layer of supernatant collected using wide-mouthed pipette tips. DNA is precipitated from the supernatant by incubation in 95% ethanol on ice for 1 h. DNA threads are spooled onto a glass hook, washed in 75% ethanol containing 0.2 M sodium acetate for 10 min, air-dried for 5 min and resuspended in TE buffer. Five µl RNAse A is added to the samples and incubated at 37° C. for 1 h.

For quantification of genomic DNA, gel electrophoresis is performed using a 0.8% agarose gel in 1×TBE buffer. One microliter of the samples are fractionated alongside 200, 400, 600 and 800 ng µl$^{-1}$λ uncut DNA markers.

Example 4

Gene Targeting

This example provides methods and constructs used to produce a targeted modification to a polynucleotide integrated in the host genome. The example describes the targeting of a stably introduced transgene, as well as the targeting of an endogenous gene.

A. Targeted Modification of a Transgene

BMS cells were stably transformed with a gusA expression vector as described in Example 3A. The gusA transgene is described in Example 2A, part i. The 5' and 3' regions of the transgene each have one SphI site which result in a 6.0-6.5 kb fragment upon SphI restriction enzyme digestion. PCR primers hybridizing to intron 1 and intron 2 amplify a 0.7 kb DNA fragment. GUS expression can be measured by several standard methods known in the art, such as a quantitative fluorimetric assay as described in (Jefferson et al. (1987) *EMBO J.* 6:3901-3907).

The introduced gusA transgene was used as a target for modification. A targeting vector was designed which replaces gusA exon 1 with a bar selectable marker gene containing a SphI site. Restriction digestion with SphI now results in a 2.3 kb DNA fragment. PCR amplification with the primers directed to introns 1 and 2 generates a 1.1 kb band. Removal of the gusA exon 1 eliminates GUS expression. The gusA target modifying polynucleotide shared a total of about 2 kb homology with the gusA target.

Calli transformed with the gusA targeting vector were sequentially screened as follows: bar$^+$ calli were selected on Basta. These bar$^+$ calli represent all transformation events. Basta-resistant calli were further screened for GUS activity using a fluorimetric assay to identify putative gene targeting events (see Table 7 below). Random integration events should be bar$^+$, GUS$^+$ while gene targeting events should be bar$^+$, GUS$^-$. Some GUS$^-$ events could be generated by gene silencing, therefore putative gene targeting events, along with controls were further analyzed by PCR with primers directed to introns 1 and 2. The loss of the 0.7 kb band is diagnostic of a gene targeting event. Cells with randomly integrated targeting vector were GUS$^+$, bar$^+$, with PCR products of 1.1 kb and 0.7 kb. Cells comprising a gene targeted modification were GUS$^-$, bar$^+$, with a PCR product of 1.1 kb only, for example events CD4 and CF5. Selected events were further evaluated by Southern analysis of genomic DNA digested with SphI using a gusA exon 2 probe confirmed the absence of a ~6.0-6.5 kb band and the presence of a 2.3 kb band in gene targeting events. While not all putative events were fully characterized, of 364 Basta-resistant calli generated 2 gene targeting events were fully confirmed using the process described above. Therefore, the frequency of gene targeting is at least 5.5× 10$^{-3}$, which corresponds well with observations in *Arabidopsis* (Puchta et al. (1996) *PNAS* 93:5055-5060).

TABLE 7

Gene targeted knockout of GUS expression

| | GUS expression (nmol MU/min/PCV BMS cells) Time (min) | | | | | | |
|---|---|---|---|---|---|---|---|
| Cell Line | 0 | 15 | 28 | 51 | 83 | 108 | 136 |
| BMS control | 14 | 21 | 22 | 38 | 43 | 43 | 40 |
| FLG75 | 27 | 272 | 511 | 873 | 1374 | 1856 | 2202 |
| CD4 | 18 | 28 | 61 | 91 | 119 | 134 | 124 |
| CF5 | 28 | 42 | 68 | 88 | 116 | 148 | 158 |
| AC4 | 23 | 64 | 191 | 302 | 428 | 561 | 678 |

BMS control = Untransformed BMS cells used as negative control
FLG75 = gusA target line used as positive control
CD4 = gene targeting event, confirmed by PCR
CF5 = gene targeting event, confirmed by PCR
AC4 = random integrant, gene silencing B. Targeted Modification of an Endogenous Gene Point mutations in acetohydroxy-acid synthase (AHAS) can be introduced to confer either a sulfonylurea or imidazolinone herbicide resistance phenotype in plants. The following examples describe the targeted modification of tobacco and maize genes to confer herbicide resistance.

i. Tobacco

Transformation, selection, and characterization of AHAS gene targeting events can be done as described in Lee et al. (1990) *Plant Cell* 2:415-425 using the modified vector pAGS182BVrep described in Example 2B, as well as the original control and targeting vectors used. Gene targeting frequency can be measured by comparing the frequency of targeted modification with vector pAGS182BVrep to the frequency with vector pAGS182BV.

ii. Maize

Transformation with AHAS targeting vectors of Example 2B can be done as described in Example 3C. Selection, and characterization of AHAS gene targeting events can be done as described in Zhu et al. (1999) *PNAS* 96:8768-8773. Gene targeting events should exhibit herbicide resistance while random integration events should be herbicide sensitive. Gene targeting frequency can be measured by comparing the frequency of targeted modification with the vectors of Example 2B to the frequency with control vectors lacking either the origin of replication or the functional replicase expression cassette.

Example 5

Crossing-Mediated Gene Targeting

This example provides methods of gene targeting by sexually crossing individual plants. Crossing plants results in gene targeting events in the developing embryos. The endogenous acetohydroxy-acid synthase (AHAS; E.C. 4.1.3.18), a key enzyme in the synthesis of the branched chain amino acids, is targeted to be converted to a mutated form that imparts resistance to an imidazolinone herbicide.

In this example, two transgenic plant lines are developed. The first transgenic line comprises a FLP recombinase expression cassette, and the endogenous AHAS gene. The second transgenic line comprises an integrated AHAS gene targeting vector flanked by FRT-sites. By crossing these two lines, the targeting vector is excised by FLP recombinase wherein it can generate AHAS gene targeted modification resulting in an imidazolinone herbicide resistance phenotype in the progeny.

A. Recombinase Transgenic Lines

The FLP-expression cassette is introduced into a maize plant comprising the endogenous AHAS gene, to produce a transgenic event. This construct contains a selection cassette (UBI::bar::pinII) and a cassette for constitutive-expression of a recombinase (UBI::moFLP::pinII) both within an *Agrobacterium* binary vector. This cassette is transformed into a maize inbred (for example the Pioneer inbred PHN46) using *Agrobacterium*-mediated transformation as described in Example 3C, and Bialaphos selection is used to recover transgenic events. Transgenic events are assessed for single-copy integration using Southern analysis, and further analyzed for FLP activity (see for example WO 99/25841). Single-copy, FLP-active events are regenerated, the plants grown to maturity, and selfed or outcrossed to produce transgenic seed.

B. Targeting Vector Transgenic Lines

The second construct is also an *Agrobacterium* transformation vector. Inside the T-borders of this construct are the molecular components necessary for crossing-base homologous recombination, the targeting vector. The targeting vector is described in Example 2C.

The targeting vector is transformed into immature embryos from the PHN46 inbred, and Bialaphos selection is used to recover transgenic events. The Bialaphos-resistant transformants are screened for single-copy integration and these events are regenerated. The resulting plants are selfed or outcrossed to produce transgenic seed.

C. Crossing and Target Modification

Using stable transformants from the two transgenic lines, crosses are made between the events produced with the above two constructs. These crosses can be made using T0 transgenic plants, or with any progeny generation of plants (T1, T2 ... Tn). For example, T1 seed from both transformants is planted and grown to maturity. Upon crossing, the FLP recombinase activity provided by the first transgenic line results in excision of the FRT-flanked targeting vector from the copy of the genome that came from the second transgenic line. When the FRT sites recombine to circularize the cassette, the LIR promoter sequence is juxtaposed to the replicase gene, resulting in replicase expression. The circularized targeting vector replicates, enhancing homologous recombination between the mutant-AHAS and the endogenous AHAS sequence. The result of this homologous recombination is the targeted modification of the endogenous AHAS sequence to the mutant form which confers resistance to imidazolinone herbicides.

Progeny plants containing such as modified AHAS locus are screened by germinating seedlings on 0.7 µM imazethapyr (AC263, 499, or Pursuit, technical grade, American Cyanamid), upon which herbicide-resistant plants are easily distinguished from wild-type plants (i.e. with an unaltered AHAS gene). Using this method, it is expected that the mutant-AHAS herbicide-resistance phenotype will be conferred (via homologous recombination) at much higher frequencies in the resulting progeny (relative to a non-replicating control targeting vector).

D. Variations

Variations on this crossing-based strategy can also be incorporated. Examples include using inducible and/or developmental or tissue-specific promoters to control expression of either the recombinase or the replicase genes, using larger regions of homology (i.e. between the target sequence and the target-modifying sequence in the two respective plants to be crossed), or controlling replicase activity by using variants selected for decreased efficacy. Replication can also be controlled by using single replicase component-genes from geminiviruses in which replicase functions have evolved in separate genes (for example, using the AL1 gene from the AL1, AL2, AL3 replicase complex in Tomato Golden Mosaic Virus, see Hanley-Bowdoin et al. (1990) *PNAS (USA)* 87(4): 1446-1450).

In another variation, one transgenic line can be produced which comprises the integrated targeting vector and a recombinase expression cassette under control of an inducible promoter. This transgenic line can be crossed to a non-transgenic line, and recombinase expression induced such that the progeny of the cross comprise gene targeted modifications in a non-transgenic background. Using the gene target of the current example, AHAS, these progeny could be easily screened.

In other variations the targeting vector is flanked by the terminal elements of transposons. In these cases, a transposase is provided to excise the targeting vector.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. A method for gene targeting in a plant cell comprising:
   (a) providing the plant cell, wherein the plant cell comprises a target polynucleotide endogenous to the plant cell, wherein the target polynucleotide is a non-coding region of the genome;
   (b) providing a non-circular targeting vector to the plant cell, wherein the targeting vector comprises a target modifying polynucleotide and a geminiviral origin of replication, wherein the target modifying polynucleotide has at least 75-150 bp of homology to the target polynucleotide;
   (c) providing an appropriate viral replicase, wherein the replicase binds to the geminiviral origin of replication to stimulate replication of the targeting vector, whereby homologous recombination between the target modifying polynucleotide and the target polynucleotide produces a modified target polynucleotide; and
   (d) recovering a plant cell comprising the modified target polynucleotide integrated into its genome.

2. The method of claim 1 wherein the targeting vector further comprises a replicase-encoding polynucleotide operably linked to a promoter.

3. The method of claim 2 wherein the replicase-encoding polynucleotide is operably linked to a constitutive promoter.

4. The method of claim 2 wherein the replicase-encoding polynucleotide is operably linked to an inducible promoter.

5. The method of claim 1 wherein the plant cell is from a monocot or a dicot.

6. The method of claim 5 wherein the plant cell is selected from the group consisting of maize, rice, wheat, oats, barley, sorghum, millet, soybean, canola, *Brassica*, alfalfa, sunflower, safflower, *Arabidopsis*, cotton, and tobacco.

7. The method of claim 1 further comprising generating a plant comprising the modified target polynucleotide integrated into its genome.

8. A method for gene targeting in a plant comprising:
   (a) providing a target plant comprising an endogenous target polynucleotide, wherein the target polynucleotide is a non-coding region of the genome, wherein the target plant comprises a targeting vector comprising a target modifying polynucleotide and a geminiviral origin of replication, wherein the target modifying polynucleotide has at least 75-150 bp of homology to the target polynucleotide;
   (b) providing a donor plant comprising an appropriate viral replicase;
   (c) sexually crossing the donor plant and the target plant, wherein the viral replicase binds to the geminiviral origin of replication to stimulate replication of the targeting vector, whereby homologous recombination between the target modifying polynucleotide and the target polynucleotide produces a modified target polynucleotide; and
   (d) recovering seed having the modified target polynucleotide integrated into its genome.

9. The method of claim 8 wherein the plant is a monocot or dicot.

10. The method of claim 9 wherein the plant is selected from the group consisting of maize, rice, wheat, oats, barley, sorghum, millet, soybean, canola, *Brassica*, alfalfa, sunflower, safflower, *Arabidopsis*, cotton, and tobacco.

* * * * *

UNITED STATES PATENT AND TRADEMARK OFFICE
CERTIFICATE OF CORRECTION

PATENT NO. : 7,608,752 B2 Page 1 of 1
APPLICATION NO. : 11/533381
DATED : October 27, 2009
INVENTOR(S) : Lyznik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 290 days.

Signed and Sealed this

Twelfth Day of October, 2010

David J. Kappos
*Director of the United States Patent and Trademark Office*